(12) United States Patent
Nagayasu et al.

(10) Patent No.: US 9,840,672 B2
(45) Date of Patent: Dec. 12, 2017

(54) ZSM-22 ZEOLITE, HYDROISOMERIZATION CATALYST AND METHOD FOR PRODUCING SAME, AND METHOD FOR PRODUCING HYDROCARBON

(71) Applicant: JX NIPPON OIL & ENERGY CORPORATION, Tokyo (JP)

(72) Inventors: Yoshiyuki Nagayasu, Tokyo (JP); Kazuaki Hayasaka, Tokyo (JP); Mayumi Yokoi, Tokyo (JP); Koshi Takahama, Tokyo (JP)

(73) Assignee: JX NIPPON OIL & ENERGY CORPORATION, Tokyo (JP)

( * ) Notice: Subject to any disclaimer, the term of this patent is extended or adjusted under 35 U.S.C. 154(b) by 368 days.

(21) Appl. No.: 14/388,525

(22) PCT Filed: Mar. 29, 2013

(86) PCT No.: PCT/JP2013/059659
§ 371 (c)(1),
(2) Date: Sep. 26, 2014

(87) PCT Pub. No.: WO2013/147218
PCT Pub. Date: Oct. 3, 2013

(65) Prior Publication Data
US 2015/0057478 A1    Feb. 26, 2015

(30) Foreign Application Priority Data

Mar. 30, 2012  (JP) .................. 2012-079872
Oct. 2, 2012   (JP) .................. 2012-220813

(51) Int. Cl.
*C10G 45/62*    (2006.01)
*C10G 45/64*    (2006.01)
(Continued)

(52) U.S. Cl.
CPC ............ *C10G 45/62* (2013.01); *B01J 29/068* (2013.01); *B01J 29/7484* (2013.01); *C07C 5/03* (2013.01);
(Continued)

(58) Field of Classification Search
CPC .............................. C10G 45/62; C10G 45/64
See application file for complete search history.

(56) References Cited

U.S. PATENT DOCUMENTS 5,282,958 A    2/1994  Santilli et al.
8,372,263 B2   2/2013  Hayasaka
(Continued)

FOREIGN PATENT DOCUMENTS

CN    101715368    5/2010
CN    102333592    1/2012
(Continued)

OTHER PUBLICATIONS

Huybrecths et al., "Bifunctional catalytic isomerization of decane over MTT-type aluminosilicate zeolite crystals with siliceous rim," *Journal of Catalysis*, vol. 239, pp. 451-459, 2006.
(Continued)

*Primary Examiner* — Sharon Pregler
*Assistant Examiner* — Alyssa L Cepluch
(74) *Attorney, Agent, or Firm* — Greenblum & Bernstein, P.L.C.

(57) ABSTRACT

A method for producing a hydroisomerization catalyst includes a first step of preparing a support precursor by heating a mixture containing an ion-exchanged zeolite and a binder, the ion-exchanged zeolite being prepared by ion-exchanging an organic template-containing zeolite which contains an organic template and has a one-dimensional pore structure including a 10-membered ring in a solution containing ammonium ions and/or protons, at a temperature of 250 to 350° C. under $N_2$ atmosphere, and a second step of preparing a hydroisomerization catalyst, which is prepared
(Continued)

by calcining a catalyst precursor, the catalyst precursor being prepared based on the support precursor containing a platinum salt and/or a palladium salt, at a temperature of 350 to 400° C. in an atmosphere containing molecular oxygen, the hydroisomerization catalyst containing a support which includes a zeolite and carries platinum and/or palladium.

5 Claims, 3 Drawing Sheets

(51) Int. Cl.
*B01J 29/068* (2006.01)
*B01J 29/74* (2006.01)
*C07C 5/03* (2006.01)
*C07C 5/27* (2006.01)
*C07C 7/04* (2006.01)

(52) U.S. Cl.
CPC .............. *C07C 5/2775* (2013.01); *C07C 7/04* (2013.01); *C10G 45/64* (2013.01); *B01J 2229/186* (2013.01); *B01J 2229/42* (2013.01); *C07C 2529/06* (2013.01); *C07C 2529/068* (2013.01)

(56) References Cited

U.S. PATENT DOCUMENTS 8,758,596 B2   6/2014  Hayasaka et al.
2010/0181229 A1   7/2010  Hayasaka
2011/0270010 A1 * 11/2011  Hayasaka ............ B01J 29/7261
                                                              585/850
2013/0008827 A1   1/2013  Nagayasu et al.

FOREIGN PATENT DOCUMENTS

| EP | 1 061 118 | 12/2000 | |
|---|---|---|---|
| JP | 07-157774 | 6/1995 | |
| JP | 2001-031980 | 2/2001 | |
| JP | 2011-005446 | 1/2011 | |
| JP | 2011-074067 | 4/2011 | |
| KR | 2010-0041791 | 4/2010 | |
| WO | 2010/074215 | 7/2010 | |
| WO | WO 2010074215 A1 * | 7/2010 | ......... B01J 29/7261 |
| WO | 2011/122446 | 10/2011 | |

OTHER PUBLICATIONS

Zhao et al., "Synthesis of ZSM-48, zeolites and their catalytic performance in C4-olefin cracking reacitons," *Applied Catalysis A: General*, vol. 29, pp. 167-174, 2006.
International Search Report of Patent Application No. PCT/JP2013/059659, mailed Jun. 18, 2013; with an English translation thereof.
English translation of International Preliminary 9, 2014. Report on Patentability for PCT/JP2013/059659, which was mailed on Oct.
Office Action issued in Korea Counterpart Patent Appl. No. 10-2014-7029257, dated Dec. 7, 2015.
Office Action issued in Chinese Patent Application No. 201380017856.3, dated Aug. 13, 2015.

* cited by examiner

ZSM-22 ZEOLITE, HYDROISOMERIZATION CATALYST AND METHOD FOR PRODUCING SAME, AND METHOD FOR PRODUCING HYDROCARBON

TECHNICAL FIELD

The present invention relates to a hydroisomerization catalyst and a method for producing the same. In addition, the present invention relates to a method for dewaxing hydrocarbon oil using the hydroisomerization catalyst, a method for producing hydrocarbon, and a method for producing lubricant base oil.

BACKGROUND ART

Among petroleum products, for example, lubricants, light gas oils, jet fuels, and the like are products that the cold flow property is considered to be important. Therefore, it is required that wax components, such as normal paraffin, which may degrade the fluidity in a low temperature condition, and isoparaffin, which has a few branches, are entirely or partially eliminated from base oil used in such products, or that such wax components are converted into components other than wax components. In recent years, hydrocarbons prepared by the Fischer Tropsch synthetic process (hereinafter simply referred to as "FT synthetic oil") has attracted attention as feedstock used in producing lubricant or fuel because FT synthetic oil contains no environmental burden-substance, such as sulfur compounds, however, such hydrocarbons contain a large content of wax components.

As a dewaxing technique for eliminating wax components from hydrocarbon oil, for example, a method for extracting wax components by means of a solvent, such as liquefied propane or methyl ethyl ketone (MEK), has been known. However, in addition to requiring high costs, the following problems may arise in this method, such that the type of applicable feedstock is limited, and that the product yield is restricted by the type of the feedstock.

On the other hand, as a dewaxing technique for converting wax components contained in hydrocarbon oil into non-wax components, catalytic dewaxing has been known, for example, in which hydrocarbon oil is contacted with a catalyst known as a bifunctional catalyst, which has a hydrogenation-dehydrogenation function and an isomerization function, in the presence of hydrogen to isomerize normal paraffin contained in hydrocarbon into isoparaffin. As a bifunctional catalyst used in catalytic dewaxing, a catalyst containing molecular sieves including solid acids, particularly zeolites, and group 8 to 10 or group 6 metals of the periodic table have been known, and in particular, a catalyst in which the above-described metal is supported on the molecular sieve has been known.

Catalytic dewaxing is effective as a method for improving the fluidity of hydrocarbon oil in a low temperature condition, and it is necessary to achieve a sufficiently high degree of conversion of normal paraffins in order to produce a fraction applicable as lubricant base oil and fuel base oil. However, the above-described catalyst used in catalytic dewaxing has a hydrocarbon cracking function in addition to an isomerization function, and therefore, in catalytic-dewaxing hydrocarbon oil, lightening of hydrocarbon oil may develop as the degree of conversion of normal paraffins rises, which makes it difficult to efficiently produce desired fractions. In particular, in producing high-quality lubricant base oil for which high viscosity index and low pour point are required, it is very difficult to economically produce a fraction to be produced by catalytic-dewaxing hydrocarbon oil, and accordingly, synthetic base oils, such as poly-α-olefins, have often been used in the field concerned.

However, in recent years, in the field of producing lubricant base oil and fuel base oil, particularly in the field of producing lubricant base oil, production of group II (viscosity index of 80 or greater and below 120; saturates of 90% by mass or greater; and sulfur content of 0.03% by mass or lower), group III (viscosity index of 120 or greater; saturates of 90% by mass or greater; and sulfur content of 0.03% by mass or lower), and group III+ base oil (viscosity index of 140 or greater; saturates of 90% by mass or greater; and sulfur content of 0.03% by mass or lower), which are classified as grades of lubricants specified by the American Petroleum Institute (API), using hydroprocessing, has become more and more widespread. Under these circumstances, in order to achieve a desired isoparaffin fraction from hydrocarbon oil including wax components with a high yield, a catalyst having an inhibited cracking activity and a high isomerization reaction activity in relation to hydrocarbons, i.e., a hydroisomerization catalyst having an excellent isomerization selectivity, is required.

Attempts have been made to improve the isomerization selectivity of a catalyst used in catalytic dewaxing. For example, the following Patent Literature 1 discloses a process for producing a dewaxed lubricant, in which a straight-chain hydrocarbon material or a hydrocarbon material having a few branches having 10 or more carbon atoms is contacted, under an isomerization condition, with a catalyst which includes molecular sieves containing group VIII metals of the periodic table and having middle-size one-dimensional pores, the dimension of crystallite of which not exceeding 0.5 µm, i.e., molecular sieves such as ZSM-22, ZSM-23, ZSM-48, and the like.

Note that a zeolite constituting a hydroisomerization catalyst is produced by hydrothermal synthesis in the presence of an organic compound known as "organic template", which usually includes an amino group, ammonium group, and the like, to construct a predetermined pore structure. The synthesized zeolite is calcined at the temperature of 550° C. or higher, for example, in an atmosphere containing molecular oxygen to eliminate organic templates contained therein, as discussed in the final paragraph of "Item 2.1. Materials", page 453 of the following Non Patent Literature 1. Typically, the calcined zeolite is then ion-exchanged to become an ammonium type zeolite in an aqueous solution containing ammonium ions, for example, as described in "Item 2.3. Catalytic experiments", page 453 of the following Non Patent Literature 1. The ion-exchanged zeolite further carries group 8 to 10 metal components of the periodic table. The zeolite supporting the metal component is then charged into a reactor after being dried and having undergone steps such as extruding, and the like if necessary, and typically is calcined at a temperature of about 400° C. in an atmosphere containing molecular oxygen, and further undergoes reduction at a similar temperature by means of hydrogen and the like; thus a catalyst activity of a bifunctional catalyst is impaired.

In a recently proposed method, in order to further improve the isomerization selectivity of a hydroisomerization catalyst, a hydrothermally synthesized zeolite is ion-exchanged in a state in which organic templates are contained, instead of calcining such zeolite at the above-described high temperature, to produce a hydroisomerization catalyst based on the ion-exchanged zeolite (see the following Patent Literature 2, for example).

CITATION LIST

Patent Literature

Patent Literature 1: U.S. Pat. No. 5,282,958
Patent Literature 2: Japanese Patent Application Laid-Open No. 2010-155187

Non Patent Literature

Non Patent Literature 1: J. A. Martens et al., J. Catal. 239 (2006), page 451

SUMMARY OF INVENTION

Technical Problem

If the isomerization selectivity of a hydroisomerization catalyst can be further increased, useful hydrocarbons, such as lubricant base oil, can be more efficiently produced.

Under these circumstances, the present invention is directed to provide a hydroisomerization catalyst with a high isomerization selectivity and a method for producing the same, and a ZSM-22 zeolite capable of implementing the hydroisomerization catalyst with a high isomerization selectivity and a method for producing the same. The present invention is also directed to provide a method for dewaxing hydrocarbon oil using the hydroisomerization catalyst, a method for producing hydrocarbon, and a method for producing lubricant base oil.

Solution to Problem

According to an aspect of the present invention, a first method for producing a hydroisomerization catalyst includes a first step of preparing a support precursor by heating a mixture containing an ion-exchanged zeolite and a binder, the ion-exchanged zeolite being prepared by ion-exchanging an organic template-containing zeolite which contains an organic template and has a one-dimensional pore structure including a 10-membered ring in a solution containing ammonium ions and/or protons, at a temperature of 250 to 350° C. under $N_2$ atmosphere, and a second step of preparing a hydroisomerization catalyst, which is prepared by calcining a catalyst precursor, the catalyst precursor being prepared based on the support precursor including a platinum salt and/or a palladium salt, at a temperature of 350 to 400° C. in an atmosphere containing molecular oxygen, the hydroisomerization catalyst containing a support which includes a zeolite and carries platinum and/or palladium.

According to the first production method for producing a hydroisomerization catalyst according to the present invention, which includes the above-described steps, a hydroisomerization catalyst with a high isomerization selectivity can be produced.

The inventors consider that the above-described effect can be achieved due to the following reasons. If ion-exchanged zeolites containing an organic template are calcined in an atmosphere containing molecular oxygen, e.g., in the air, water is generated by an oxidation reaction, and aluminium is denatured (for example, four-coordinate aluminum changes its structure to become six-coordinate aluminium) because aluminium contained in the zeolite is steamed at a high temperature due to the generated water; the cracking activity is considered to increase due to the above-described cause. In the first step according to the present invention in which the mixture is heated in the temperature range under an $N_2$ atmosphere, the organic templates can be moderately eliminated without generating water as a byproduct even if the organic templates are thermally cracked; and the steaming at a high temperature, which may occur due to the water generated from water that has been absorbed by the zeolite or water generated based on a silanol group is prevented, and accordingly, the increase of the six-coordinate aluminium is sufficiently inhibited. It can be considered that even if some organic templates remain after the first step, organic templates can be moderately eliminated while preventing the steaming of aluminium at a high temperature because the oxidized platinum and/or palladium function as a calcining catalyst as a result of the second step, in which a catalyst precursor including a platinum salt and/or a palladium salt is calcined under the above-described conditions. As described above, the inventors consider that the hydroisomerization catalyst with a high isomerization selectivity is implemented because it is enabled by the present invention to eliminate organic templates not completely but moderately while inhibiting the denaturation of aluminium contained in the zeolite and while improving the isomerization selectivity by carrying out ion exchange in a state in which the zeolite contains the organic templates. Note that if the calcining is carried out under temperature conditions by which the results may exceed the upper limit values and the organic templates are completely eliminated, the reactant is sufficiently diffused into the micropores, and the cracking reaction is considered to easily develop in the micropores, and on the other hand, if the results becomes below the lower limit value of the temperature condition, a large content of organic templates may remain inside the zeolite pores, which is considered to inhibit the development of the isomerization reaction.

In order to achieve a high isomerization selectivity in the hydroisomerization reaction of normal paraffins, it is preferable that the zeolite be at least one zeolite selected from the group consisting of: a ZSM-22 zeolite; a ZSM-23 zeolite; an SSZ-32 zeolite; and a ZSM-48 zeolite.

In addition, considering the activity, the isomerization selectivity, and the persistence of the activity of the catalyst to be treated according to the present embodiment, it is preferable that the platinum salt be tetraammineplatinum dinitrate and the palladium salt be tetraamminepalladium nitrate.

In order to achieve a higher isomerization selectivity, it is preferable that the binder includes at least one inorganic oxide selected from the group consisting of silica; alumina; and alumina-silica.

The present invention is capable of providing a first hydroisomerization catalyst, which can be produced by the first production method for producing a hydroisomerization catalyst according to the present invention.

The present invention also provides a second hydroisomerization catalyst, which is a hydroisomerization catalyst including: a support including a zeolite having a one-dimensional pore structure including a 10-membered ring and a binder; and platinum and/or palladium supported on the support, the zeolite being derived from an ion-exchanged zeolite prepared by ion-exchanging an organic template-containing zeolite, which contains an organic template and has a one-dimensional pore structure including a 10-membered ring, in a solution containing ammonium ions and/or protons, and the catalyst having a carbon content of 0.4 to 2.5% by mass.

Hereinbelow, the carbon content of the hydroisomerization catalyst is calculated by analyzing the catalyst by an in-oxygen airflow combustion-infrared ray absorption method. More specifically, a catalyst is combusted in an oxygen airflow by means of a carbon/sulfur analysis apparatus (e.g., EMIA-920V produced by HORIBA, Ltd.) and the carbon content is determined by means of the infrared ray absorption method.

According to the second hydroisomerization catalyst of the present invention, which includes the above-described configuration, a high isomerization selectivity in a hydroisomerization reaction of normal paraffins can be achieved.

The inventors infer that the above-described effect of the present invention is achieved by the second hydroisomerization catalyst because: a moderate content of organic templates contained in the ion-exchanged zeolite remains in the zeolite pores because the carbon content of the catalyst is set within the range; accordingly, a sufficient isomerization selectivity is achieved; and as a result, the isomerization selectivity can sufficiently develop while the cracking reaction of normal paraffins is sufficiently inhibited.

For the second hydroisomerization catalyst of the present invention, it is preferable that the volume of micropores per unit mass of the catalyst be 0.02 to 0.11 cm$^3$/g and that the volume of micropores per unit mass of the zeolite contained in the catalyst be 0.04 to 0.12 cm$^3$/g.

The present invention also provides a third hydroisomerization catalyst, which is a hydroisomerization catalyst including: a support including a zeolite having a one-dimensional pore structure including a 10-membered ring and a binder; and platinum and/or palladium supported on the support, a volume of micropores per unit mass of the catalyst being 0.02 to 0.11 cm$^3$/g, wherein the zeolite is derived from an ion-exchanged zeolite prepared by ion-exchanging an organic template-containing zeolite, which contains an organic template and has a one-dimensional pore structure including a 10-membered ring, in a solution containing ammonium ions and/or protons, and a volume of micropores per unit mass of the zeolite contained in the catalyst is 0.04 to 0.12 cm$^3$/g.

Hereinbelow, the volume of micropores per unit mass of the hydroisomerization catalyst is calculated by a method known as a nitrogen adsorption measurement method. More specifically, for the catalyst, the volume of micropores per unit mass thereof is calculated by analyzing an isothermal line of physical nitrogen adsorption and desorption measured at a liquid nitrogen temperature (−196° C.), i.e., by analyzing an isothermal line of nitrogen adsorption measured at a liquid nitrogen temperature (−196° C.) by a t-plot method. Furthermore, the volume of micropores per unit mass of the zeolite contained in the catalyst is calculated by the above-described nitrogen adsorption measurement method.

Hereinbelow, a "micropore" refers to a "pore having a diameter of 2 nm or less" as defined by the International Union of Pure and Applied Chemistry (IUPAC).

According to the third hydroisomerization catalyst of the present invention, which includes the above-described configuration, a high isomerization selectivity in a hydroisomerization reaction of normal paraffins can be achieved.

The inventors infer that the above-described effect of the present invention is achieved by the third hydroisomerization catalyst because: the volume of micropores per unit mass of the catalyst controlled within the above-described range brings about the sufficient isomerization selectivity; and furthermore, if the volume of micropores per unit mass of the zeolite contained in the catalyst is controlled within the above-described range in this case, a moderate content of organic templates contained in the ion-exchanged zeolite are considered to be remaining in the zeolite pores; and therefore, the isomerization selectivity can sufficiently develop while sufficiently inhibiting the cracking reaction of normal paraffins.

The ZSM-22 zeolite according to the present invention can be produced by ion-exchanging a crystalline aluminosilicate having a one-dimensional pore structure including a 10-membered ring, synthesized in the presence of an organic template containing 1,8-diamino octane, in a solution containing ammonium ions and/or protons in a state in which the organic template is contained, wherein in a powder X-ray diffraction pattern of calcined powder, a ratio of intensity $I_1/I_2$ between a peak intensity $I_1$ appearing at $2\theta=8.1\pm0.5°$ and a peak intensity $I_2$ appearing at $2\theta=20.3\pm0.5°$ is 1 or smaller; an external surface area of the calcined powder, which is determined by the nitrogen adsorption measurement method is 40 m$^2$/g or larger; and the volume of micropores of the calcined powder, which is determined by the nitrogen adsorption measurement method, is 0.01 to 0.11 cm$^3$/g.

According to the ZSM-22 zeolite of the present invention, which is used as a material of the carriage contained in the hydroisomerization catalyst, the isomerization selectivity of the catalyst can be improved.

The method for producing a ZSM-22 zeolite according to the present invention includes a step of ion-exchanging a crystalline aluminosilicate having a one-dimensional pore structure including a 10-membered ring, synthesized by a hydrothermal synthesis method from a mixture containing a silica source, an alumina source, and an organic template containing 1,8-diamino octane, in a solution containing ammonium ions and/or protons in a state in which the organic template is contained.

The second method for producing a hydroisomerization catalyst according to the present invention includes: a first step of producing a support precursor by calcining a support material at a temperature of 250 to 350° C., the support material containing a ZSM-22 zeolite according to the present invention or a ZSM-22 zeolite produced by the method of the present invention, or a heated ZSM-22 zeolite, which is prepared by heating the ZSM-22 zeolite according to the present invention or the ZSM-22 zeolite produced by the method of the present invention at a temperature of 350° C. or lower; and a second step of producing a hydroisomerization catalyst, which is prepared by calcining a catalyst precursor, the catalyst precursor being prepared based on the support precursor including a platinum salt and/or a palladium salt, at a temperature of 350 to 400° C. in an atmosphere containing molecular oxygen, the hydroisomerization catalyst containing a support which includes a ZSM-22 zeolite and carries platinum and/or palladium.

According to the second method for producing a hydroisomerization catalyst of the present invention, which includes the above-described steps, a hydroisomerization catalyst with a high isomerization selectivity in a hydroisomerization reaction of normal paraffins can be produced.

The present invention provides a fourth hydroisomerization catalyst, which is produced by the second method for producing a hydroisomerization catalyst according to the present invention.

For the fourth hydroisomerization catalyst according to the present invention, it is preferable that the carbon content of the catalyst be 0.5 to 3.5% by mass.

The carbon content of the hydroisomerization catalyst is calculated by analyzing the catalyst by an in-oxygen airflow combustion-infrared ray absorption method. More specifically, a catalyst is combusted in an oxygen airflow by means of a carbon/sulfur analysis apparatus (e.g., EMIA-920V produced by HORIBA, Ltd.) and the carbon content is determined by means of the infrared ray absorption method.

For the fourth hydroisomerization catalyst according to the present invention, it is preferable that the volume of micropores per unit mass of the catalyst be 0.02 to 0.12 cm$^3$/g.

Hereinbelow, the volume of micropores per unit mass of the calcined powder of the zeolite and the volume of micropores per unit mass of the catalyst are calculated by a method known as the nitrogen adsorption measurement method. More specifically, for each measurement sample, the volume of micropores (cm$^3$/g) is calculated by analyzing an isothermal line of physical nitrogen adsorption and desorption measured at a liquid nitrogen temperature (−196° C.), i.e., by analyzing an isothermal line of nitrogen adsorption measured at a liquid nitrogen temperature (−196° C.) by a t-plot method.

In the method for dewaxing hydrocarbon oil according to the present invention, a hydrocarbon oil containing normal paraffins having 10 or more carbon atoms is contacted with the first, the second, the third, or the fourth hydroisomerization catalyst according to the present invention in the presence of hydrogen to convert some of or all the normal paraffins into isoparaffins.

In the method for producing hydrocarbon according to the present invention, a hydrocarbon feedstock containing normal paraffins having 10 or more carbon atoms is contacted with the first, the second, the third, or the fourth hydroisomerization catalyst according to the present invention.

In the method for producing lubricant base oil according to the present invention, a hydrocarbon feedstock containing normal paraffins having 10 or more carbon atoms is contacted with the first, the second, the third, or the fourth hydroisomerization catalyst in the presence of hydrogen under conditions by which the conversion of normal paraffins, which is defined by the following Expression (I), becomes substantially 100% by mass.

$$\text{Normal paraffin conversion (\%)} = \left[1 - \frac{\begin{pmatrix}\text{Total mass of normal paraffins equal}\\\text{to or greater than } Cn \text{ contained in}\\\text{contacted hydrocarbon feedstock}\end{pmatrix}}{\begin{pmatrix}\text{Total mass of normal paraffins equal}\\\text{to or greater than } Cn \text{ contained in}\\\text{hydrocarbon feedstock yet to be}\\\text{contacted}\end{pmatrix}}\right] \times 100 \quad (I)$$

where Cn is the lowest number of carbon atoms of normal paraffins having 10 or more carbon atoms contained in the hydrocarbon feedstock yet to be contacted.

According to the method for producing lubricant base oil according to the present invention, hydrocarbons suitable as a lubricant base oil can be produced at a high yield by hydrotreating a hydrocarbon feedstock by means of the hydroisomerization catalyst according to the present invention under the above-described conditions.

In the method for producing lubricant base oil according to the present invention, a hydrocarbon feedstock can be further hydrofinished and vacuum-distilled after the hydrocarbon feedstock is contacted with the hydroisomerization catalyst.

It is preferable that the hydrocarbon feedstock be at least one selected from the group consisting of: atmospheric residues; vacuum residues; a vacuum gas oil; a slack wax; and a Fischer Tropsch synthetic wax.

Advantageous Effect of Invention

According to the present invention, a hydroisomerization catalyst with a high isomerization selectivity and a method for producing the same, and a ZSM-22 zeolite capable of implementing the hydroisomerization catalyst with a high isomerization selectivity and a method for producing the same can be provided. The present invention is also capable of providing a method for dewaxing hydrocarbon oil using the hydroisomerization catalyst, a method for producing hydrocarbon, and a method for producing lubricant base oil.

DESCRIPTION OF EMBODIMENTS

Figure 1:
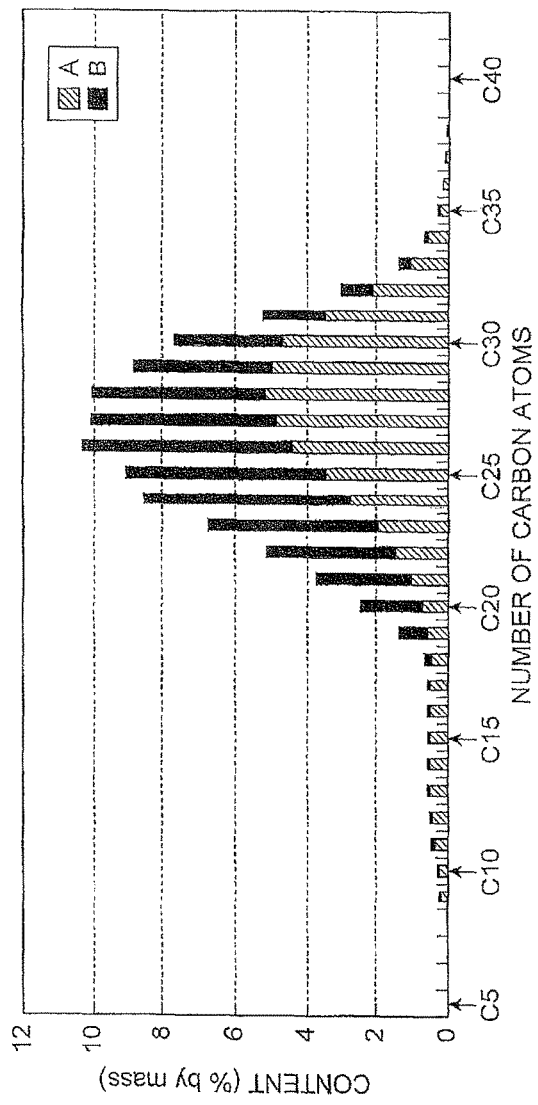
FIG. 1 is a graph illustrating a distribution of the number of carbon atoms of a stock wax.

Hydroisomerization Catalyst According to First Embodiment of the Present Invention Characteristics of a hydroisomerization catalyst according to the first embodiment are impaired thereto by producing the same by a specific method. Hereinbelow, the hydroisomerization catalyst according to the first embodiment will be described with reference to preferred embodiments for producing the same.

The method for producing a hydroisomerization catalyst according to the present embodiment includes: a first step of preparing a support precursor by heating a mixture containing an ion-exchanged zeolite and a binder, the ion-exchanged zeolite being prepared by ion-exchanging an organic template-containing zeolite which contains an organic template and has a one-dimensional pore structure including a 10-membered ring in a solution containing ammonium ions and/or protons, at a temperature of 250 to 350° C. under N$_2$ atmosphere; and a second step of preparing a hydroisomerization catalyst, which is prepared by calcining a catalyst precursor, the catalyst precursor being prepared based on the support precursor including a platinum salt and/or a palladium salt, at a temperature of 350 to 400° C. in an atmosphere containing molecular oxygen, the hydroisomerization catalyst containing a support which includes a zeolite and carries platinum and/or palladium.

In order to achieve a high isomerization activity and an inhibited cracking activity of normal paraffins in a hydroisomerization reaction at the same time, the organic template-containing zeolite according to the present embodiment has a one-dimensional pore structure including a 10-membered ring Examples of such zeolites include AEL, EUO, FER, HEU, MEL, MFI, NES, TON, MTT, WEI,*MRE, and SSL-32. Note that each of the above-described three-letter terms refer to a skeletal structure code defined by the Structure Commission of the International Zeolite Association for each of classified molecular sieve-type zeolites. In addition, zeolites having the same topology are comprehensively designated by the same code.

For the organic template-containing zeolite, considering the isomerization activity and the inhibited cracking activity, among the above-described zeolites having a one-dimensional pore structure including a 10-membered ring, zeolites having the TON structure and the MIT structure, a ZSM-48 zeolite, which is a zeolite having the *MRE structure, and an SSZ-32 zeolite are preferable. For the zeolite having the TON structure, the ZSM-22 zeolite is more preferable; and for the zeolite having the MTT structure, the ZSM-23 zeolite is more preferable.

The organic template-containing zeolite is thermally synthesized from a silica source, an alumina source, and organic templates added to constitute the predetermined pore structure by means of a known method.

The organic template is an organic compound having an amino group, an ammonium group, and the like and selected on the basis of the structure of the zeolite to be synthesized, and it is preferable that the organic template be an amine derivative. More specifically, it is preferable that the organic template be at least one selected from the group consisting of alkylamine, alkyl diamine, alkyl triamine, alkyl tetramine, pyrrolidine, piperazine, amino piperazine, alkyl pentamine, alkyl hexamine, and derivatives thereof. The carbon number of the alkyl can be 4 to 10, and preferably be 6 to 8.

It is preferable that a molar ratio between silicon and aluminum ([Si]/[Al]) (hereinafter simply referred to as an "Si/Al ratio") contained in the organic template-containing zeolite having a one-dimensional pore structure including a 10-membered ring be 10 to 400, and more preferably be 20 to 350. If the Si/Al ratio is less than 10, the activity of normal paraffin in relation to conversion becomes high, but this ratio is not preferable because the selectivity to isomerization into isoparaffin may degrade and the cracking reaction occurring due to the rise in the reaction temperature tends to increase abruptly in this case. On the other hand, if the Si/Al ratio is greater than 400, this ratio is not preferable because it becomes difficult to achieve a high catalytic activity required to convert the normal paraffin.

The synthesized, preferably washed and dried organic template-containing zeolite usually contains alkali metal cations as counter cations, and organic templates are contained within the pore structure. It is preferable that the zeolite containing the organic template used in producing the hydroisomerization catalyst according to the present invention be a synchronized zeolite, i.e., a zeolite that has not been subjected to calcining for eliminating organic templates contained therein.

The organic template-containing zeolite then undergo ion exchange in a solution containing ammonium ions and/or protons. The counter cations contained in the organic template-containing zeolite are exchanged with ammonium ions and/or protons by the ion exchange treatment. At the same time, some of the organic templates contained in the organic template-containing zeolite are eliminated.

It is preferable that the solution used in the ion exchange treatment be a solution prepared with a solvent containing at least 50% by volume of water, and more preferably be an aqueous solution. Examples of the compound which supplies ammonium ions in the solution include various inorganic and organic ammonium salts, such as ammonium chlorides, ammonium sulfates, ammonium nitrates, ammonium phosphates, ammonium acetates, and the like. On the other hand, as the compound which supplies protons to the solution, mineral acids, such as hydrochloric acids, sulfuric acids, nitric acids are usually utilized. The ion-exchanged zeolite (in the present embodiment, an ammonium zeolite) prepared by ion-exchanging an organic template-containing zeolite releases ammonium in the later stage of calcining the catalytic component; and the counter cations become protons to filially constitute Bronsted acid sites. It is preferable to use ammonium ions as the cationic species used in the ion exchange. It is preferable that the content of the ammonium ions and/or protons contained in the solution be set so that the content of the ammonium ions and/or protons contained in the solution becomes 10 to 1,000 equivalents in relation to the total content of the counter cations and the organic templates contained in the organic template-containing zeolite to be used.

The above-described ion exchange treatment can be carried out for a powdered organic template-containing zeolite support, or otherwise can be carried out for an extruded body obtained by extruding a mixture prepared by combining an inorganic oxide, which is a binder, with the organic template-containing zeolite prior to the ion exchange treatment. However, the extruded body may easily degrade and become powdered if the extruded body is subjected to the ion exchange treatment without calcining the same, and therefore, it is preferable to carry out the ion exchange treatment for a powdered organic template-containing zeolite.

It is preferable to perform the ion exchange treatment by a usual method, i.e., by a method in which an organic template-containing zeolite is immersed in a solution containing ammonium ions and/or protons, preferably an aqueous solution, and the mixture is agitated or fluidized. Furthermore, it is preferable that the agitation or the fluidization be carried out in a heated state to increase the efficiency of the ion exchange. In the present invention, a method in which the aqueous solution is heated and the ion exchange is carried out under boiling reflux conditions is particularly preferable.

Furthermore, from a point of view of increasing the efficiency of the ion exchange, it is preferable that the solution be exchanged with a new solution once or twice or more during the ion exchange of the zeolite by means of the solution, and it is more preferable that the solution be exchanged with a new solution once or twice. If the solution is to be exchanged once, the efficiency of the ion exchange can be increased in the following manner, for example: the organic template-containing zeolite is immersed in a solution containing ammonium ions and/or protons; the solution is then heated under reflux for 1 to 6 hours; then the solution is exchanged with a new solution; and then the solution is further heated under reflux for 6 to 12 hours.

By carrying out the ion exchange treatment, substantially all the counter cations, such as alkali metal, in the zeolite can be exchanged with ammonium ions and/or protons. On the other hand, although some of the organic templates included in the zeolite are eliminated by the ion exchange treatment, it is generally difficult to completely eliminate the organic templates and some of the other organic templates may remain inside the zeolite.

In the present embodiment, a mixture containing the ion-exchanged zeolite and the binder is heated at 250 to 350° C. under a nitrogen atmosphere to prepare a support precursor.

For the mixture containing the ion-exchanged zeolite and the binder, an extruded body obtained by extruding a composition prepared by combining an inorganic oxide, which is the binder, with the ion-exchanged zeolite obtained by the above-described method is preferable. The purpose of combining an inorganic oxide with the ion-exchanged zeolite is to improve the mechanical strength of the support prepared by calcining the extruded body (particularly the powdered support) to a practicable level, and the inventors have found that the selection of the type of the inorganic oxide has an influence on the isomerization selectivity of the hydroisomerization catalyst. In this respect, as the above-described inorganic oxide, at least one inorganic oxide selected from the group consisting of alumina, silica, titania, boria, zirconia, magnesia, ceria, a zinc oxide, a phosphorus oxide, and a complex oxide which is an oxide of a combination of two or more of the above-described oxides is used. Among them, in order to further improve the isomerization selectivity of the hydroisomerization catalyst, silica and alumina are preferable, and alumina is more preferable. In addition, the "complex oxide which is an oxide of a combination of two or more of the above-described oxides" is a complex oxide including at least two of alumina, silica, titania, boria, zirconia, magnesia, ceria, a zinc oxide, and a phosphorus oxide, and a complex oxide mainly having alumina containing alumina component of 50% by mass in relation to the complex oxide as the main component thereof is preferable; and alumina-silica is particularly more preferable.

It is preferable that the combination ratio between the ion-exchanged zeolite and the inorganic oxide in the composition be 10:90 to 90:10, and more preferably be 30:70 to 85:15, as the ratio of the ion-exchanged zeolite to the inorganic oxide. If this ratio is less than 10:90, the ratio is not preferable because the activity of the hydroisomerization catalyst tends to become insufficiently high in this case. On the other hand, if this ratio exceeds 90:10, the ratio is not preferable because the mechanical strength of the support prepared by extruding and calcining the composition tends to become insufficiently high in this case.

The method for combining the inorganic oxide with the ion exchange zeolite is not limited to a particular method, and a usual method can be employed, in which, for example, a viscous fluid is prepared by adding liquid, such as a proper amount of water, to the powder of the ion-exchanged zeolite and the inorganic oxide and the resulting viscous fluid is kneaded by means of a kneading machine and the like.

The composition containing the ion-exchanged zeolite and the inorganic oxide or the viscous fluid containing the composition is extruded by a method such as extrusion extruding, and is then preferably be dried, to be reduced to particulate extruded body. The shape of the extruded body is not particularly limited, and examples of the shape of the extruded body include a cylindrical shape, a pellet-like shape, a spherical shape, a deformed cylindrical shape having a trefoil or quatrefoil cross section, and the like. The dimension of the extruded body is not particularly limited, and considering the ease of handling the extruded body and the packing density of the extruded body in the reactor, it is preferable that the extruded body have a major axis of about 1 to 30 mm and a minor axis of about 1 to 20 mm.

In the present embodiment, it is preferable to prepare the support precursor by heating the extruded body prepared by the above-described method at the temperature of 250 to 350° C. under $N_2$ atmosphere. Preferable heating time is 0.5 to 10 hours, and the heating time of 1 to 5 hours is more preferable.

In the present embodiment, if the heating temperature is below 250° C., a large amount of organic templates may remain, and thus the zeolite micropores may be clogged by the remaining templates. In this case, an isomerization active site is considered to exist in the vicinity of a micropore mouth, and accordingly, the reaction substrate cannot be diffused into the micropores due to the clogging of the micropores, which may inhibit the development of the isomerization reaction because the active site is covered, and as a result, a sufficiently high conversion degree of conversion of normal paraffin tends to become difficult to achieve. On the other hand, if the heating temperature is higher than 350° C., the isomerization selectivity of the resulting hydroisomerization catalyst may not sufficiently improve.

The lower limit temperature set in preparing the support precursor by heating the extruded body is preferably 280° C. or higher. The upper limit temperature set in this preparation is preferably 330° C. or lower.

In the present embodiment, it is preferable to heat the mixture so that some of the organic templates contained in the extruded body remain. More specifically, it is preferable to set heating conditions so that the carbon content of the hydroisomerization catalyst prepared after the following calcining is carried out after the metal is supported becomes 0.4 to 2.5% by mass. Furthermore, it is preferable to set the heating conditions so that the volume of the micropores becomes 0.02 to 0.11 $cm^3/g$ per unit mass of the hydroisomerization catalyst prepared after the following calcining is carried out after the metal is supported and that the volume of the micropores becomes 0.04 to 0.12 $cm^3/g$ per unit mass of the zeolite contained in the catalyst.

Subsequently, a catalyst precursor prepared on the basis of the support precursor including a platinum salt and/or a palladium salt is calcined at the temperature of 350 to 400° C., preferably 380 to 400° C., and more preferably 400° C., in an atmosphere containing molecular oxygen to prepare a hydroisomerization catalyst in which platinum and/or palladium is supported on the support containing the zeolite. Note that the description "in an atmosphere containing molecular oxygen" refers to a contact of the precursor with gas containing oxygen gas, preferably with air, in particular. The time for the calcining is preferably 0.5 to 10 hours, and more preferably 1 to 5 hours.

Examples of the platinum salts include chloroplatinic acids, tetraammineplatinum dinitrates, dinitroamino platinum, tetraammine dichloroplatinum, and the like. If a chloride salt is used, hydrochloric acids may be generated at the time of reaction, which may cause apparatus corrosion, and therefore a tetraammineplatinum dinitrate which is not a chloride salt but a platinum salt containing platinum having a high dispersion property is preferable.

Examples of the palladium salt include palladium chlorides, tetraammine palladium nitrates, diaminopalladium nitrates, and the like. If a chloride salt is used, hydrochloric acids may be generated at the time of reaction, which may cause apparatus corrosion, and therefore a tetraammine palladium nitrate which is not a chloride salt but a palladium salt containing palladium having a high dispersion property is preferable.

The content of the active metal supported in the support including a zeolite according to the present embodiment is preferably 0.001 to 20% by mass, more preferably 0.01 to 5% by mass, in relation to the mass of the support. If the content of the metal supported is less than 0.001% by mass, it becomes difficult to impart a predetermined hydrogenation/dehydrogenation function. On the other hand, if the content of the metal supported is greater than 20% by mass, this content is not preferable because the phenomenon of lightening may easily develop due to the cracking of hydrocarbon on the active metal, and as a result, the yield of the fraction to be produced tends to degrade, and moreover, the costs for the catalyst may increase.

In addition, if the hydroisomerization catalyst according to the present embodiment is used for the hydroisomerization of hydrocarbon oil containing a large content of sulfur-containing compounds and/or nitrogen-containing compounds, considering the persistence of the catalytic activity, it is preferable that the active metal include: a nickel/cobalt combination; a nickel/molybdenum combination; a cobalt/molybdenum combination; a nickel/molybdenum/cobalt combination; a nickel/tungsten/cobalt combination, and the like. The content of the above-described metals supported in the support is preferably 0.001 to 50% by mass, and more preferably 0.01 to 30% by mass, in relation to the mass of the support.

In the present embodiment, it is preferable to calcin the catalyst precursor so that the organic templates remaining in the support precursor further remain. More specifically, it is preferable to set the heating conditions so that the carbon content of the hydroisomerization catalyst to be prepared becomes 0.4 to 2.5% by mass. Furthermore, it is preferable to set the heating conditions so that the volume of the micropores becomes 0.02 to 0.11 cm$^3$/g per unit mass of the hydroisomerization catalyst to be prepared and that the volume of the micropores becomes 0.04 to 0.12 cm$^3$/g per unit mass of the zeolite contained in the catalyst.

The carbon content of the hydroisomerization catalyst is calculated by analyzing it by an in-oxygen airflow combustion-infrared ray absorption method. More specifically, a catalyst is combusted in an oxygen airflow by means of a carbon/sulfur analysis apparatus (e.g., EMIA-920V produced by HORIBA, Ltd.) and the carbon content is determined by means of the infrared ray absorption method.

The volume of the micropores per unit mass of the hydroisomerization catalyst is calculated by a method known as a nitrogen adsorption measurement method. More specifically, for the catalyst, the volume of micropores in the catalyst is calculated by analyzing an isothermal line of physical nitrogen adsorption and desorption measured at a liquid nitrogen temperature (−196° C.), i.e., by analyzing an isothermal line of nitrogen adsorption measured at a liquid nitrogen temperature (−196° C.) by a t-plot method. In addition, the volume of the micropores per unit mass of the zeolite contained in the catalyst is calculated by the above-described nitrogen adsorption measurement.

The volume of micropores per unit mass of the zeolite contained in the catalyst $V_z$ can be calculated by the following expression if the binder contains no volume of micropores:

$$V_Z = V_c / M_z \times 100$$

where $V_c$ is a value of the volume of the micropores per unit mass of the hydroisomerization catalyst, and $M_z$ is the ratio of content (% by mass) of the zeolite contained in the catalyst.

It is preferable that the hydroisomerization catalyst according to the first embodiment undergo reduction after the above-described calcining process, preferably after filling the hydroisomerization catalyst into the reactor in which the hydroisomerization reaction is to occur. More specifically, it is preferable that the hydroisomerization catalyst according to the first embodiment be subjected to reduction for 0.5 to 5 hours in an atmosphere containing molecular hydrogen, preferably under a hydrogen gas flow, preferably at 250 to 500° C., more preferably at 300 to 400° C. By executing the above-described steps, high activity for dewaxing hydrocarbon oil can be more securely imparted to the catalyst.

In another aspect according to the first embodiment of the present invention, a hydroisomerization catalyst includes: a support including a zeolite having a one-dimensional pore structure including a 10-membered ring and a binder; and platinum and/or palladium supported on the support, the zeolite being derived from an ion-exchanged zeolite prepared by ion-exchanging an organic template-containing zeolite, which contains an organic template and has a one-dimensional pore structure including a 10-membered ring, in a solution containing ammonium ions and/or protons, and the catalyst having a carbon content of 0.4 to 2.5% by mass.

In yet another aspect the first embodiment according to of the present invention, a hydroisomerization catalyst includes: a support including a zeolite having a one-dimensional pore structure including a 10-membered ring and a binder; and platinum and/or palladium supported on the support, a volume of micropores per unit mass of the catalyst being 0.02 to 0.11 cm$^3$/g, wherein the zeolite is derived from an ion-exchanged zeolite prepared by ion-exchanging an organic template-containing zeolite, which contains an organic template and has a one-dimensional pore structure including a 10-membered ring, in a solution containing ammonium ions and/or protons, and a volume of micropores per unit mass of the zeolite contained in the catalyst is 0.04 to 0.12 cm$^3$/g. In the present embodiment, it is preferable that the carbon content of the catalyst be 0.4 to 2.5% by mass.

The hydroisomerization catalyst can be produced by the above-described method. The carbon content of the catalyst, the volume of micropores per unit mass of the catalyst, and the volume of micropores per unit mass of the zeolite contained in the catalyst can be set within the above-described ranges, respectively, by appropriately adjusting the following conditions: the content of the ion-exchanged zeolite to be combined in a mixture containing the ion-exchanged zeolite and binder; the heating condition for the mixture under N$_2$ atmosphere; and the heating condition for the catalyst precursor in an atmosphere containing molecular oxygen.

<ZSM-22 Zeolite>

The ZSM-22 zeolite according to the present invention can be produced by ion-exchanging a crystalline aluminosilicate having a one-dimensional pore structure including a 10-membered ring, synthesized in the presence of an organic template containing 1,8-diamino octane, in a solution containing ammonium ions and/or protons in a state in which the organic template is contained, wherein in a powder X-ray diffraction pattern of calcined powder a ratio of intensity $I_1/I_2$ between a peak intensity $I_1$ appearing at 2θ=8.1±0.5° and a peak intensity $I_2$ appearing at 2θ20.3±0.5° is 1 or smaller; an external surface area of the calcined powder, which is determined by the nitrogen adsorption measurement method, is 40 m$^2$/g or larger; and the volume of micropores of the calcined powder, which is determined by the nitrogen adsorption measurement method, is 0.01 to 0.11 cm$^3$/g.

The code name "ZSM-22" of the ZSM-22 zeolite herein denotes a TON-zeolite specified by the International Zeolite Association (IZA).

For the condition for preparing the calcined powder, if a the ZSM-22 zeolite is to be used as a support material of the catalyst, condition for calcinating a support material containing the ZSM-22 zeolite can be set.

A method for producing a ZSM-22 zeolite according to the present invention will be described.

The crystalline aluminosilicate having a one-dimensional pore structure including a 10-membered ring can be hydrothermally synthesized from a mixture which contains a silica source, an alumina source, and organic templates containing 1,8-diamino octane.

The crystalline aluminosilicate has a crystallizability, which represents that a crystalline aluminosilicate is a substance spatially arrayed with a repeated pattern; i.e., that a crystalline aluminosilicate is able to diffract incident X rays.

The hydrothermal synthesis method refers to a method for synthesizing a compound carried out at high temperatures and pressures in the presence of hot water or for allowing the crystal of the compound to grow; more specifically, in the hydrothermally synthesis method, a raw material and water are heated in a sealed pressure tight case. In the present embodiment, a known method can be used.

Examples of the silica source include: colloidal silica; water glass; aerosil; aerogel; silica sol; silica gel; powder silica; silicate; and the like.

Examples of the alumina source include: aluminum sulfate; aluminum nitrate; aluminum chloride; boehmite; pseudo boehmite; aluminum hydroxide; and the like.

For the organic template, compounds other than 1,8-diamino octane can be concurrently used within the range in which the effects of the present invention are not impaired. Examples of such compounds include: 1,6-diaminohexane; and the like.

For the condition for the hydrothermal synthesis, a temperature of 50 to 300° C. and a pressure of atmospheric pressure to 2 MPa can be set.

It is preferable that a molar ratio between silicon and aluminum ([Si]/[Al]) (hereinafter simply referred to as an "Si/Al ratio") included in the crystalline aluminosilicate having a one-dimensional pore structure including a 10-membered ring be 10 to 400, and more preferably be 20 to 350. If the Si/Al ratio is less than 10, the activity of normal paraffin in relation to conversion becomes high, but this ratio is not preferable because the selectivity to isomerization into isoparaffin may degrade and the cracking reaction occurring due to the rise in the reaction temperature tends to increase abruptly in this case. On the other hand, if the Si/Al ratio is greater than 400, this ratio is not preferable because it becomes difficult to achieve a high catalytic activity required to convert the normal paraffin.

The synthesized, preferably washed and dried crystalline aluminosilicate usually contains alkali metal cations as counter cations, and organic templates including 1,8-diamino octane are included in the pore structure.

The crystalline aluminosilicate then undergo ion exchange in a solution containing ammonium ions and/or protons in a state including organic templates. It is preferable that the crystalline aluminosilicate be powder synthesized and dried as-is: i.e., it is preferable that the crystalline aluminosilicate be powder that has not undergone a calcining treatment for eliminating the organic templates included in the crystalline aluminosilicate.

The counter cations contained in the organic template-containing zeolite are exchanged with ammonium ions and/or protons by the ion exchange treatment. At the same time, some of the organic templates contained in the organic template-containing zeolite are eliminated.

It is preferable that the solution used in the ion exchange treatment be a solution prepared with a solvent containing at least 50% by volume of water, and more preferably be an aqueous solution. Examples of the compound which supplies ammonium ions in the solution include various inorganic and organic ammonium salts, such as ammonium chlorides, ammonium sulfates, ammonium nitrates, ammonium phosphates, ammonium acetates, and the like. On the other hand, as the compound which supplies protons to the solution, mineral acids, such as hydrochloric acids, sulfuric acids, nitric acids are usually utilized. The ion-exchanged zeolite (in the present embodiment, an ammonium zeolite) prepared by ion-exchanging an organic template-containing zeolite releases ammonium in the later stage of calcining the catalytic component; and the counter cations become protons to finally constitute Bronsted acid sites. It is preferable to use ammonium ions as the cationic species used in the ion exchange. It is preferable that the content of the ammonium ions and/or protons contained in the solution be set so that the content of the ammonium ions and/or protons contained in the solution becomes 10 to 1,000 equivalents in relation to the total content of the counter cations and the organic templates contained in the organic template-containing zeolite to be used.

The above-described ion exchange treatment can be carried out for a powdered crystalline aluminosilicate support, or otherwise can be carried out for an extruded body obtained by extruding a mixture prepared by combining an inorganic oxide, which is a binder, with the crystalline aluminosilicate prior to the ion exchange treatment. However, the extruded body may easily degrade and become powdered if the extruded body is subjected to the ion exchange treatment without calcining the same, and therefore, it is preferable to carry out the ion exchange treatment for a powdered crystalline aluminosilicate.

It is preferable to perform the ion exchange treatment by a usual method, i.e., by a method in which an organic template-containing zeolite is immersed in a solution containing ammonium ions and/or protons, preferably an aqueous solution, and the mixture is agitated or fluidized. Furthermore, it is preferable that the agitation or the fluidization be carried out in a heated state to increase the efficiency of the ion exchange. In the present invention, a method in which the aqueous solution is heated and the ion exchange is carried out under boiling reflux conditions is particularly preferable.

Furthermore, from a point of view of increasing the efficiency of the ion exchange, it is preferable that the solution be exchanged with a new solution once or twice or more during the ion exchange of the zeolite by means of the solution, and it is more preferable that the solution be exchanged with a new solution once or twice. If the solution is to be exchanged once, the efficiency of the ion exchange can be increased in the following manner, for example: the organic template-containing zeolite is immersed in a solution containing ammonium ions and/or protons; the solution is then heated under reflux for 1 to 6 hours; then the solution is exchanged with a new solution; and then the solution is further heated under reflux for 6 to 12 hours.

By carrying out the ion exchange treatment, substantially all the counter cations, such as alkali metal, in the crystalline aluminosilicate can be exchanged with ammonium ions and/or protons. On the other hand, although some of the organic templates included in the crystalline aluminosilicate are eliminated by the ion exchange treatment, it is generally difficult to completely eliminate the organic templates, and some of the other organic templates may remain inside the crystalline aluminosilicate.

To dry up the ion-exchanged crystalline aluminosilicate, the crystalline aluminosilicate can be heated at a temperature of 350° C. or lower, preferably at 100° C. or lower, and more preferably at 80° C. or lower. For an atmosphere for drying, a nitrogen atmosphere or an atmosphere containing molecular oxygen, such as an air atmosphere, can be used. The ion-exchanged crystalline aluminosilicate can be dried by the above-described heating, and thus the ease of handling of the crystalline aluminosilicate can be improved.

The ZSM-22 zeolite according to the present invention is produced in the above-described manner.

In the ZSM-22 zeolite according to the present invention, in a powder X-ray diffraction pattern of calcined powder, a ratio of intensity $I_1/I_2$ between a peak intensity $I_1$ appearing at $2\theta=8.1\pm0.5°$ and a peak intensity $I_2$ appearing at $2\theta=20.3\pm0.5°$ is 1 or smaller.

The powder X-ray diffraction pattern is measured with an "X-ray Diffractometer RINT 2500" (a product of Rigaku Corporation) under the following conditions:

X-ray source: Cu-Kα line;
Voltage: 50 kV; and
Current: 200 mA

In the powder X-ray diffraction pattern of the zeolite, a peak appearing at $2\theta=8.1°$ represents a (110) plane and a peak appearing at $2\theta=20.3°$ represents a (021) plane. In a ZSM-22 zeolite, the (110) plane is considered to be an index indicating the crystallizability in the major axis (L), and the (021) plane is considered to be an index indicating the crystallizability in the minor axis (D). If the intensity ratio $I_1/I_2$ is 1 or less, this index is considered to suggest that the ZSM-22 zeolite is a crystallite.

Considering that the ZSM-22 zeolite is a crystallite, it is preferable that the above-described intensity ratio $I_1/I_2$ be 0.9 or less, and more preferably 0.7 or less.

For the ZSM-22 zeolite according to the present invention, the external surface area determined by the nitrogen adsorption measurement method for the calcined powder is 40 $m^2/g$ or greater, and in order to inhibit the cracking reaction, it is preferable that the external surface area be 50 $m^2/g$ or greater, and more preferably be 70 $m^2/g$ or greater.

The above-described external surface area is determined as an external surface area per unit mass of the ZSM-22 zeolite by analyzing an isothermal line of physical nitrogen adsorption and desorption measured at a liquid nitrogen temperature (−196° C.), i.e., by analyzing an isothermal line of nitrogen adsorption measured at a liquid nitrogen temperature (−196° C.) by a t-plot method.

For the ZSM-22 zeolite according to the present invention, the volume of micropores of the calcined powder, which is determined by the nitrogen adsorption measurement method, is 0.01 to 0.11 $cm^3/g$, and in order to inhibit the cracking reaction, a volume of micropores of 0.01 to 0.10 $cm^3/g$ is preferable, and a volume of micropores of 0.01 to 0.05 $cm^3/g$ is more preferable.

The volume of micropores is determined as a volume of micropores per unit mass of the ZSM-22 zeolite by analyzing an isothermal line of physical nitrogen adsorption and desorption measured at a liquid nitrogen temperature (−196° C.), i.e., by analyzing an isothermal line of nitrogen adsorption measured at a liquid nitrogen temperature (−196° C.) by a t-plot method.

For the condition for preparing the calcined powder, if the ZSM-22 zeolite is to be used as a support material of the catalyst, condition for calcining a support material containing the ZSM-22 zeolite can be set. For example, if an extruded body prepared by extruding a mixture containing the ZSM-22 zeolite and a binder is used as a support material of the catalyst, the heating conditions for calcining the extruded body can be selected as the calcined powder preparation condition.

For the ZSM-22 zeolite according to the present invention, it is preferable that the external surface area, which is determined by the nitrogen adsorption measurement method for the calcined powder prepared by drying the ZSM-22 zeolite at 60° C. and then calcining the ZSM-22 zeolite at 300° C. for 3 hours under nitrogen atmosphere, be 40 $m^2/g$ or larger, more preferably 50 $m^2/g$ or larger, and yet more preferably 70 $m^2/g$ or larger. In addition, it is preferable that the volume of micropores determined by the nitrogen adsorption measurement method for the calcined powder prepared by drying the ZSM-22 zeolite at 60° C. and then calcining the ZSM-22 zeolite at 300° C. for 3 hours under nitrogen atmosphere, be 0.01 to 0.11 $cm^3/g$, more preferably 0.01 to 0.10 $cm^3/g$, and yet more preferably 0.01 to 0.05 $cm^3/g$.

Hydroisomerization Catalyst According to Second Embodiment of the Present Invention Characteristics of a hydroisomerization catalyst according to the second embodiment are impaired thereto by producing the same by a specific method. Hereinbelow, the hydroisomerization catalyst according to the second embodiment will be described with reference to preferred embodiments for producing the same.

The method for producing a hydroisomerization catalyst according to the present embodiment includes: a first step of producing a support precursor by calcining a support material at a temperature of 250 to 350° C., the support material containing the ZSM-22 zeolite according to the present invention or a heated ZSM-22 zeolite, which is prepared by heating the ZSM-22 zeolite according to the present invention at a temperature of 350° C. or lower; and a second step of producing a hydroisomerization catalyst, which is prepared by calcining a catalyst precursor, the catalyst precursor being prepared based on the support precursor including a platinum salt and/or a palladium salt, at a temperature of 350 to 400° C. in an atmosphere containing molecular oxygen, the hydroisomerization catalyst containing a support which includes a ZSM-22 zeolite and carries platinum and/or palladium.

In the first step, it is preferable to prepare the support precursor by calcining a mixture including the ZSM-22 zeolite as a support material and a binder at a temperature of 250 to 300° C. For an atmosphere for the first step, a nitrogen atmosphere or an atmosphere containing molecular oxygen, such as an air atmosphere, can be used.

For the mixture including the ZSM-22 zeolite and the binder, an extruded body is preferable, which is prepared by extruding a composition prepared by combining an inorganic oxide, which is a binder, with the ZSM-22 zeolite produced by the above-described method. The purpose of combining an inorganic oxide with the ZSM-22 zeolite is to improve the mechanical strength of the support prepared by calcining the extruded body (particularly the powdered support) to a practicable level, and the inventors have found that the selection of the type of the inorganic oxide has an influence on the isomerization selectivity of the hydroisomerization catalyst. In this respect, as the above-described inorganic oxide, at least one inorganic oxide selected from the group consisting of alumina, silica, titania, boria, zirconia, magnesia, ceria, a zinc oxide, a phosphorus oxide, and a complex oxide which is an oxide of a combination of two or more of the above-described oxides is used. Among them, in order to further improve the isomerization selectivity of the hydroisomerization catalyst, silica and alumina are preferable, and alumina is more preferable. In addition, the "complex oxide which is an oxide of a combination of two or more of the above-described oxides" is a complex oxide including at least two of alumina, silica, titania, boria, zirconia, magnesia, ceria, a zinc oxide, and a phosphorus oxide, and a complex oxide mainly having alumina containing alumina component of 50% by mass in relation to the complex oxide as the main component thereof is preferable; and alumina-silica is particularly more preferable.

It is preferable that the combination ratio between the ZSM-22 zeolite and the inorganic oxide in the composition be 10:90 to 90:10, and more preferably be 30:70 to 85:15, as the ratio of the ZSM-22 zeolite to the inorganic oxide. If this ratio is less than 10:90, the ratio is not preferable because the activity of the hydroisomerization catalyst tends to become insufficiently high in this case. On the other hand, if this ratio exceeds 90:10, the ratio is not preferable because the mechanical strength of the support prepared by extruding and calcining the composition tends to become insufficiently high in this case.

The method for combining the inorganic oxide with the ZSM-22 zeolite is not limited to a particular method, and a usual method can be employed, in which a viscous fluid is prepared by adding liquid, such as a proper amount of water, to the powder of the ZSM-22 zeolite and the inorganic oxide and the resulting viscous fluid is kneaded by means of a kneading machine and the like.

The composition including the ZSM-22 zeolite and the inorganic oxide or the viscous fluid including the composition is extruded by a method such as extrusion extruding, and is then preferably be dried, to be reduced to particulate extruded body. The shape of the extruded body is not particularly limited, and examples of the shape of the extruded body include a cylindrical shape, a pellet-like shape, a spherical shape, a deformed cylindrical shape having a trefoil or quatrefoil cross section, and the like. The dimension of the extruded body is not particularly limited, and considering the ease of handling the extruded body and the packing density of the extruded body in the reactor, it is preferable that the extruded body have a major axis of about 1 to 30 mm and a minor axis of about 1 to 20 mm, for example.

In the present embodiment, it is preferable to prepare the support precursor by calcining the extruded body prepared by the above-described method at the temperature of 250 to 350° C. under $N_2$ atmosphere. Preferable heating time is 0.5 to 10 hours, and the heating time of 1 to 5 hours is more preferable.

In the present embodiment, if the calcining temperature is below 250° C., a large amount of organic templates may remain, and thus the zeolite micropores may be clogged by the remaining templates. In this case, an isomerization active site is considered to exist in the vicinity of a micropore mouth, and accordingly, the reaction substrate cannot be diffused into the micropores due to the clogging of the micropores, which may inhibit the development of the isomerization reaction because the active site is covered, and as a result, a sufficiently high conversion degree of conversion of normal paraffin tends to become difficult to achieve. On the other hand, if the calcining temperature is higher than 350° C., the isomerization selectivity of the resulting hydroisomerization catalyst may not sufficiently improve.

The lower limit temperature set in preparing the support precursor by calcining the extruded body is preferably 280° C. or higher. The upper limit temperature set in this preparation is preferably 330° C. or lower.

In the present embodiment, it is preferable to heat the mixture so that some of the organic templates contained in the extruded body remain. More specifically, it is preferable to set heating conditions so that the carbon content of the hydroisomerization catalyst prepared after the following calcining is carried out after the metal is supported becomes 0.5 to 3.5% by mass, preferably 0.5 to 3.0% by mass, more preferably 0.5 to 2.5% by mass, and yet more preferably 0.8 to 2.5% by mass. Furthermore, it is preferable to set the heating conditions so that the volume of the micropores becomes 0.02 to 0.12 $cm^3/g$ per unit mass of the hydroisomerization catalyst produced after the following calcining is carried out after the metal is supported and so that the volume of the micropores becomes 0.01 to 0.11 $cm^3/g$ per unit mass of the zeolite contained in the catalyst.

Subsequently, a catalyst precursor prepared on the basis of the support precursor including a platinum salt and/or a palladium salt is calcined at the temperature of 350 to 400° C., preferably 380 to 400° C., and more preferably 400° C., in an atmosphere containing molecular oxygen to prepare a hydroisomerization catalyst in which platinum and/or palladium is supported on the support containing the zeolite. Note that the description "in an atmosphere containing molecular oxygen" refers to a contact of the precursor with gas containing oxygen gas, preferably with air, in particular. The time for the calcining is preferably 0.5 to 10 hours, and more preferably 1 to 5 hours.

Examples of the platinum salts include chloroplatinic acids, tetraammineplatinum dinitrates, dinitroamino platinum, tetraammine dichloroplatinum, and the like. If a chloride salt is used, hydrochloric acids may be generated at the time of reaction, which may cause apparatus corrosion, and therefore a tetraammineplatinum dinitrate which is not a chloride salt but a platinum salt containing platinum having a high dispersion property is preferable.

Examples of the palladium salt include palladium chlorides, tetraammine palladium nitrates, diaminopalladium nitrates, and the like. If a chloride salt is used, hydrochloric acids may be generated at the time of reaction, which may cause apparatus corrosion, and therefore a tetraammine palladium nitrate which is not a chloride salt but a palladium salt containing palladium having a high dispersion property is preferable.

The content of the active metal supported in the support including a zeolite according to the present embodiment is preferably 0.001 to 20% by mass, more preferably 0.01 to 5% by mass, in relation to the mass of the support. If the content of the metal supported is less than 0.001% by mass, it becomes difficult to impart a predetermined hydrogenation/dehydrogenation function. On the other hand, if the content of the metal supported is greater than 20% by mass, this content is not preferable because the phenomenon of lightening may easily develop due to the cracking of hydrocarbon on the active metal, and as a result, the yield of the fraction to be produced tends to degrade, and moreover, the costs for the catalyst may increase.

In addition, if the hydroisomerization catalyst according to the present embodiment is used for the hydroisomerization of hydrocarbon oil containing a large content of sulfur-containing compounds and/or nitrogen-containing compounds, considering the persistence of the catalytic activity, it is preferable that the active metal include: a nickel/cobalt combination; a nickel/molybdenum combination; a cobalt/molybdenum combination; a nickel/molybdenum/cobalt combination; a nickel/tungsten/cobalt combination, and the like. The content of the above-described metals supported in the support is preferably 0.001 to 50% by mass, and more preferably 0.01 to 30% by mass, in relation to the mass of the support.

In the present embodiment, it is preferable to calcin the catalyst precursor so that the organic templates remaining in the support precursor further remain. More specifically, it is preferable to set the heating conditions so that the carbon content of the hydroisomerization catalyst produced after the following calcining is carried out after the metal is supported becomes 0.5 to 3.5% by mass, preferably 0.5 to 3.0% by mass, more preferably 0.5 to 2.5% by mass, and yet more preferably 0.8 to 2.5% by mass. Furthermore, it is preferable to set the heating conditions so that the volume of the micropores becomes 0.02 to 0.12 cm$^3$/g per unit mass of the hydroisomerization catalyst to be prepared and that the volume of the micropores becomes 0.01 to 0.11 cm$^3$/g per unit mass of the zeolite contained in the catalyst.

The carbon content of the hydroisomerization catalyst is calculated by analyzing it by an in-oxygen airflow combustion-infrared ray absorption method. More specifically, a catalyst is combusted in an oxygen airflow by means of a carbon/sulfur analysis apparatus (e.g., EMIA-920V produced by HORIBA, Ltd.) and the carbon content is determined by means of the infrared ray absorption method.

The volume of the micropores per unit mass of the hydroisomerization catalyst is calculated by a method known as a nitrogen adsorption measurement method. More specifically, for the catalyst, the volume of micropores per unit mass in the catalyst is calculated by analyzing an isothermal line of physical nitrogen adsorption and desorption measured at a liquid nitrogen temperature (−196° C.), i.e., by analyzing an isothermal line of nitrogen adsorption measured at a liquid nitrogen temperature (−196° C.) by a t-plot method. The volume of the micropores per unit mass of the catalyst is calculated by dividing the calculated volume of micropores by the content of the catalyst used in the nitrogen adsorption measurement.

It is preferable that the hydroisomerization catalyst according to the second embodiment undergo reduction after the above-described calcining process, preferably after filling the hydroisomerization catalyst into the reactor in which the hydroisomerization reaction is to occur. More specifically, it is preferable that the hydroisomerization catalyst according to the second embodiment be subjected to reduction for about 0.5 to 5 hours in an atmosphere containing molecular hydrogen, preferably under a hydrogen gas flow, preferably at 250 to 500° C., more preferably at 300 to 400° C. By executing the above-described steps, high activity for dewaxing hydrocarbon oil can be more securely imparted to the catalyst.

The inventors consider that the hydroisomerization catalyst according to the second embodiment can be provided with a high isomerization selectivity because of the contribution of the following requirements to the reduction of the cracking function of the catalyst. More specifically, the cracking function of the hydroisomerization catalyst is greatly decreased compared with that of conventional zeolite having a one-dimensional pore structure including a 10-membered ring and used in hydroisomerization catalysts because:

(1) a moderate content of 1,8-diamino octane remains because the ZSM-22 zeolite according to the present invention is synthesized by means of the specific organic templates, becomes a ZSM-22 zeolite with microcrystals and a large external surface area, and undergoes ion exchange in a state including organic templates; and (2) the phenomenon of steaming on zeolite skeletons, which may occur due to calcining, can be suppressed by heating a support material including the above-described ZSM-22 zeolite at 250 to 350° C. before supporting the active metal and at 350 to 400° C. after the active metal is supported.

<Method for Dewaxing Hydrocarbon Oil>

Now, the method for dewaxing hydrocarbon oil according to the present invention will be described below. The method for dewaxing hydrocarbon oil according to the present invention includes a step of converting some or all of normal paraffins into isoparaffins by contacting a hydrocarbon oil including normal paraffins having 10 or more carbon atoms with the hydroisomerization catalyst according to the present invention in the presence of hydrogen.

The hydrocarbon oil (oil to be treated), which is contacted in the method for dewaxing hydrocarbon oil according to the present invention is not limited to a specific type if the hydrocarbon oil includes normal paraffins having 10 or more carbon atoms, and can preferably contain normal paraffins with a carbon number of 15 or greater. More specifically, examples of such hydrocarbon oil include: relatively light distilled fractions, such as kerosenes and jet fuels; and high boiling point stocks, such as: fuel fractions or wax fractions derived from any type of crude oils, atmospheric distillation residues (atmospheric residues), vacuum tower residues, vacuum distillation residues (vacuum residues), cycle stocks, syncrudes (e.g., shale oil, tar oil, and the like), gas oil, vacuum gas oil, foots oil, and FT synthetic oil; and other heavy oils. In addition, the above-described hydrocarbon oil may contain wax components including naphthenic hydrocarbons having a long, straight chain alkyl group or a wax component including aromatic hydrocarbons as a side chain in addition to the normal paraffin.

For the hydrocarbon oil used in the present embodiment, hydrocarbon oil including hydrocarbons having 10 or more carbon atoms having a boiling point of about 180° C. or higher is particularly preferable. Hydrocarbon oil lighter than the above-described hydrocarbon oil usually contains substantially no wax components that influence the fluidity in low-temperature conditions, and therefore, it becomes difficult to achieve the effect of the present invention because the necessity to carry out dewaxing is low in this case.

On the other hand, it is especially effective to apply the dewaxing method according to the present invention to: distillate stocks containing wax components, i.e., middle distillate stocks including gas oils, kerosenes, and jet fuels; lubricant stocks; and heating oils, and in addition, other distilled fractions for which pour points and the viscosity are required to be kept within a predetermined range. Examples of such hydrocarbon oil include hydrotreated or hydrocracked oil, such as: a gas oil, a heavy gas oil, a vacuum gas oil, atmospheric residues, vacuum residues, lubricant raffinate, a lubricant stock, a bright stock, a slack wax (rough wax), a foots oil, a deoiling wax, a paraffin wax, a microcrystalline wax, petrolatum, a synthetic oil, an FT synthetic oil, high pour point polyolefins, a straight chain α-olefin wax, and the like. These can be used singly or in combinations of two or more. In particular, it is preferable that the hydrocarbon oil be at least one selected from the group consisting of: vacuum gas oil, hydrocracked vacuum gas oil, atmospheric residues, hydrocracked atmospheric residues, vacuum residues, hydrocracked vacuum residues, a bright stock, a slack wax, a dewaxed oil, a paraffin wax, a microcrystalline wax, petrolatum, and a Fischer Tropsch synthetic wax, and more preferably be at least one selected from the group consisting of: atmospheric residues, vacuum residues, a vacuum gas oil, a slack wax, and a Fischer Tropsch synthetic wax.

In the method for dewaxing hydrocarbon oil according to the present invention, examples of reaction conditions in converting at least one part of the normal paraffins into isoparaffins include the following.

A preferable hydroisomerization temperature is 200 to 450° C., and a temperature of 220 to 400° C. is more preferable. If the reaction temperature is lower than 200° C., the isomerization of normal paraffins contained in the hydrocarbon feedstock, which is a raw material, may not appropriately develop, and as a result, the wax components may tend to be insufficiently reduced or eliminated. On the other hand, if the reaction temperature is higher than 450° C., the cracking of the hydrocarbon oil becomes remarkable and the yield of the hydrocarbon to be produced tends to degrade.

For the pressure for hydroisomerization reaction, a pressure of 0.1 to 20 MPa is preferable, and a pressure of 0.5 to 15 MPa is more preferable. If the reaction pressure is below 0.1 MPa, the degradation of the catalyst may be accelerated due to cokes generated during the reaction. On the other hand, if the reaction pressure is higher than 20 MPa, an economical process may tend to be difficult to achieve because the apparatus construction costs may increase.

A liquid space velocity of the hydrocarbon oil to the catalyst is preferably 0.01 to 100 $h^{-1}$, and more preferably 0.1 to 50 $h^{-1}$. If the liquid space velocity is lower than 0.01 $h^{-1}$, the cracking of the hydrocarbon oil may excessively easily develop, and thus the production efficiency for the hydrocarbon to be produced may tend to decrease. On the other hand, if the liquid space velocity is higher than 100 $h^{-1}$, the development of the isomerization of normal paraffins contained in the hydrocarbon oil may be inhibited, and as a result, the reduction and elimination of wax components may tend to become insufficient.

A feed ratio of hydrogen and hydrocarbon oil is preferably 100 to 1,000 $Nm^3/m^3$, and more preferably 200 to 800 $Nm^3/m^3$. If the feed ratio is below 100 $Nm^3/m^3$ and if, for example, the feedstock contains sulfur compounds and nitrogen compounds, the predetermined catalytic performance may tend to become difficult to achieve because hydrogen sulfides and ammonium gas generated by desulfurization and denitrogenation reactions occurring concurrently with the isomerization reaction may be poisoned by adsorbing active metals on the catalyst. On the other hand, if the feed ratio is higher than 1,000 $Nm^3/m^3$, an economical process may tend to become difficult to achieve because a large-capacity hydrogen feeding facilities become necessary.

The degree of conversion of the normal paraffin in the hydroisomerization reaction in the method for dewaxing hydrocarbon oil according to the present invention is appropriately adjusted according to the purpose of use of the hydrocarbon to be produced.

<Method for Producing Hydrocarbon>

The method for producing hydrocarbon according to the present invention includes a step of contacting a hydrocarbon feedstock including normal paraffins having 10 or more carbon atoms with the hydroisomerization catalyst according to the present invention in the presence of hydrogen. For the hydrocarbon feedstock contacted in the method for producing hydrocarbon according to the present invention, the above-described hydrocarbon oil can be used. The reaction conditions employed in the above-described method for dewaxing hydrocarbon oil is preferable as the reaction condition in the above-described step.

<Method for Producing Lubricant Base Oil>

Now, the method for producing lubricant base oil according to the present invention will be described below. In the method for producing lubricant base oil according to the present invention, a hydrocarbon feedstock including normal paraffins having 10 or more carbon atoms is contacted with the hydroisomerization catalyst according to the present invention under conditions by which the conversion of normal paraffins, which is defined by the following Expression (I), becomes substantially 100% by mass.

$$\text{Normal paraffin conversion (\%)} = \left[1 - \frac{\left(\begin{array}{c}\text{Total mass of normal paraffins equal}\\\text{to or greater than } Cn \text{ contained in}\\\text{contacted hydrocarbon feedstock}\end{array}\right)}{\left(\begin{array}{c}\text{Total mass of normal paraffins equal}\\\text{to or greater than } Cn \text{ contained in}\\\text{hydrocarbon feedstock yet to be}\\\text{contacted}\end{array}\right)}\right] \times 100 \quad (I)$$

where Cn is the lowest number of carbon atoms of normal paraffins having 10 or more carbon atoms contained in the hydrocarbon feedstock yet to be contacted.

The condition by which the "conversion of normal paraffins . . . becomes substantially 100% by mass" means that the content of the normal paraffins included in the contacted hydrocarbon oil is 0.1% by mass or less.

The hydrocarbon feedstock contacted in the method for producing lubricant base oil according to the present invention is not limited to a specific type if the hydrocarbon feedstock includes normal paraffins having 10 or more carbon atoms, and can preferably contain hydrocarbon oil with an initial boiling point higher than that of the lubricant base oil to be desired. As the above-described stock, fractions having a boiling point in terms of atmospheric pressure is higher than 360° C., such as petroleum fractions, synthetic oil, and synthetic wax are suitable; more specifically, examples of such stocks include: atmospheric residues; heavy gas oil; vacuum residues; a vacuum gas oil; lubricant raffinate; a bright stock; a slack wax (rough wax); foot's oil; a deoiling wax; a paraffin wax; a microcrystalline wax; petrolatum; a synthetic oil; an FT synthetic oil; an FT compound wax; high pour point polyolefins; a straight chain α-olefin wax, and the like. It is particularly preferable to use atmospheric residues, a vacuum gas oil, vacuum residues, a slack wax, an FT synthetic oil, and an FT compound wax. One type of the above-described stocks can be used alone, or alternatively, two types of more of them can be used in combination. In addition, it is preferable that the above-described oil be previously treated by hydrotreating or mild hydrocracking. By carrying out the above-described treatment, sulfur-containing compounds, materials that may degrade the activity of hydroisomerization catalysts such as nitrogen-containing compounds, and materials that may degrade the viscosity index of lubricant base oil, such as aromatic hydrocarbon, naphthenic hydrocarbon, and the like, can be decreased or eliminated.

The isomerization of the normal paraffins contained in the hydrocarbon oil, i.e., the dewaxing reaction of the hydrocarbon oil, can be allowed to develop while sufficiently inhibiting the phenomenon of lightening by contacting relatively heavy hydrocarbon oil, which is a stock, with the hydroisomerization catalyst according to the present invention in the presence of hydrogen. Thus, hydrocarbon with a ratio of 90% by volume or higher of fractions having a boiling point in terms of atmospheric pressure is higher than 360° C. can be produced at a high yield. In addition, according to the method for producing lubricant base oil according to the present invention, base oil containing a large content of isomers having a branched chain structure can be produced. In particular, it is required for high quality lubricant base oil to contain 0.1% by mass or less normal paraffin, and according to the method for producing lubricant base oil of the present invention, lubricant base oil that satisfies the quality requirement can be produced at a high yield.

For the reaction condition employed in the method for producing lubricant base oil according to the present invention, the reaction condition set in the above-described method for dewaxing hydrocarbon oil is preferable.

In the hydroisomerization of hydrocarbon feedstock containing normal paraffins, the degree of conversion of normal paraffins can be usually increased by raising the reaction temperature, for example, and thus the content of normal paraffins in the reaction product to be produced can be lowered, and accordingly, the fluidity of hydrocarbon oil in low temperature conditions can be improved. However, if the reaction temperature is raised, the cracking reaction of the hydrocarbon oil, which is a stock, and an isomerization product may be promoted, and accordingly, light fractions may increase as the conversion of normal paraffins rises. The increase in the light fractions may cause the decrease of the viscosity index of hydrocarbon oil, and therefore, in order to set the performance of the lubricant base oil within a predetermined range, it is necessary to separate and eliminate the light fractions by distillation or the like. In particular, in producing the following high-performance lubricant base oil including Group II, III, and III+ oils, or the like classified as lubricant grade oils by the American Petroleum Institute (API) (specified requirements for these oils are as follows) by catalytic dewaxing of the above-described hydrocarbon feedstocks, it is required that the conversion of the normal paraffins contained in the hydrocarbon oil, which is the stock, is substantially 100%:

Group II oils: viscosity index of 80 or greater and below 120; saturates of 90% by mass or greater; and sulfur content of 0.03% by mass or lower Group III+ oils: viscosity index of 120 or greater; saturates of 90% by mass or greater; and sulfur content of 0.03% by mass or lower Group 111+ oils: viscosity index of 140 or greater; saturates of 90% by mass or greater; and sulfur content of 0.03% by mass or lower. In conventional methods for producing lubricant base oil using a catalyst for catalytic dewaxing, if a condition for substantially achieving the 100% conversion of normal paraffins is employed, the yield of the above-described high-performance lubricant base oils may become extremely low. According to the method for producing lubricant base oil according to the present invention, even if the condition for substantially achieving the 100% conversion of normal paraffins is employed in carrying out the hydrotreating step, the yield of the above-described high-performance lubricant base oils can be maintained at a high level.

Facilities for implementing the method for dewaxing hydrocarbon oil, the method for producing hydrocarbon, and the method for producing lubricant base oil according to the present invention are not limited to specific types and known facilities can be used. For reaction facilities, any of continuous flow type, batch type, and semi-batch type facilities can be used, and the continuous flow type is preferable considering the productivity and the efficiency. For a catalyst layer, any of an immobilized bed, a fluidized bed, and an agitating bed can be used, and the immobilized bed is preferable considering the facility costs and the like. A reactional phase is preferably a gas-liquid mixed phase.

In addition, in the method for dewaxing hydrocarbon oil, the method for producing hydrocarbon, and the method for producing lubricant base oil according to the present invention, the hydrocarbon oil, which is the stock to be fed, can be hydrotreated or hydrocracked at a stage prior to the dewaxing step carried out by the hydroisomerization reaction. In this case, known facilities, catalyst, and reaction conditions are used. By executing the above-described pretreatments, the activity of the hydroisomerization catalyst according to the present invention can be maintained for a long period, and in addition, environmental burden-substances contained in the products, such as sulfur-containing compounds and nitrogen-containing compounds, can be reduced.

In the method for producing hydrocarbon and method for producing lubricant base oil according to the present invention, the reaction product produced after undergoing the catalytic dewaxing, in which the hydrocarbon feedstock is contacted with the hydroisomerization catalyst according to the present invention, can be further treated by hydrofinishing, for example. The hydrofinishing can be implemented generally by contacting a product to be finished with a metal supporting hydrogenation catalyst (e.g., platinum and/or palladium supported on alumina or silica alumina) in the presence of hydrogen. By performing the hydrofinishing described above, the hue, the oxidation stability, and the like of the reaction product produced by the dewaxing step can be improved, and as a result, the product quality can be improved. The hydrofinishing can be implemented by reaction facilities provided separately from those for the dewaxing step; alternatively, the hydrofinishing can be carried out in a catalyst layer for hydrofinishing, which can be provided on a downstream side of a catalyst layer for the hydroisomerization catalyst according to the present embodiment, which is provided within the reactor for the dewaxing step.

Note that the term "isomerization" usually refers to a reaction in which the molecular structure only changes without any change in the number of carbon atoms (molecular mass) and the term "cracking" refers to a reaction in which the number of carbon atoms (molecular mass) decreases. In the isomerization dewaxing reaction which utilizes the isomerization reaction, even if cracking of hydrocarbon oils contained in the stock and products of the isomerization occurs to a degree, such degree of cracking may not become intolerable if the number of carbon atoms (molecular mass) of the product comes within a predetermined range in which the base oil to be produced can be constituted, and a cracking product can be a component of the base oil.

EXAMPLES

[Production of Hydroisomerization Catalyst]

Example A-1

<Production of ZSM-22 Zeolite>

A ZSM-22 zeolite (hereinafter simply referred to as "ZSM-22") including a crystalline aluminosilicate having the Si/Al ratio of 45 was produced by hydrothermal synthesis in the following manner.

At the start of the operation, the following four types of aqueous solutions were prepared.

Solution A: a solution prepared by dissolving 1.94 g of potassium hydroxide in 6.75 mL of deionized water.

Solution B: a solution prepared by dissolving 1.33 g of aluminum sulfate octadecahydrate in 5 mL of deionized water.

Solution C: a solution prepared by diluting 4.18 g of 1,6-hexanediamine (organic template) in 32.5 mL of deionized water.

Solution D: a solution prepared by diluting 18 g of colloidal silica (Ludox AS-40 manufactured by Grace Davison) in 31 mL of deionized water.

Then, the solution A was added to the solution B, and the mixture was agitated until aluminum components were completely dissolved.

The solution C was added to the mixed solution, then the mixed solution containing the solutions A, B, and C was intensely agitated at room temperature and the agitated mixed solution was poured into the solution D. 0.25 g of powder of ZSM-22, which had been separately synthesized as a "seed crystal" for accelerating crystallization and which had not undergone special treatment after the synthesis, was added to the mixed solution to obtain a gelled substance.

The gelled substance prepared by the above-described operation was transferred into a stainless steel autoclave reactor having an internal volume of 120 mL, the autoclave reactor was rotated on a tumbling apparatus for 60 hours in an oven kept at 150° C. at the rotation speed of about 60 rpm to run a hydrothermal synthesis reaction. After the reaction was completely run, the reactor was cooled down, opened, and dried overnight in a drier kept at 60° C., and as a result, a ZSM-22 having the Si/Al ratio of 45 was produced.

<Ion Exchange of ZSM-22 Including Organic Templates>

An ion-exchanging treatment was carried out for the ZSM-22 produced in the above-described manner in an aqueous solution containing ammonium ions by the following operations.

The ZSM-22 produced in the above-described manner was transferred into a flask, then 100 mL of 0.5 N-ammonium chloride aqueous solution for 1 g of ZSM-22 zeolite was added, and the mixture was heated under flux for 6 hours. Then the mixture was cooled down to room temperature, the supernatant liquid was removed, and the crystalline aluminosilicate was washed in the deionized water. The same amount of a 0.5 N-ammonium chloride aqueous solution of as that described above was added to the mixture again, and the mixture was heated under reflux for 12 hours.

Subsequently, solid contents were extracted by filtration, the extracted solid contents were then washed with the deionized water, dried overnight in a drier kept at 60° C. to produce an ion-exchanged $NH_4$-ZSM-22. The ZSM-22 was ion-exchanged in a state in which organic templates were contained.

<Mixing of Binder, Extruding, Calcination>

The $NH_4$-ZSM-22 produced by the above-described operation and alumina, which was used as a binder, were mixed at the mass ratio of 7:3, then a small amount of deionized water was added to the mixture, and then the mixture was kneaded. The produced viscous fluid was charged into an extruder to be extruded, and a cylindrical extruded body having the diameter of about 1.6 mm and the length of about 10 mm was prepared. This extruded body was heated at 300° C. for 3 hours under $N_2$ atmosphere, and a support precursor was produced.

<Supporting of Platinum, Calcination>

A tetraammineplatinum dinitrate $[Pt(NH_3)_4](NO_3)_2$ was dissolved in deionized water equivalent to a previously measured water absorption of the support precursor to prepare an impregnation solution. The solution was impregnated into the support precursor by an incipient wetness method, and supporting was performed so as to allow 0.3% by mass of platinum to be supported on the ZSM-22 zeolite in relation to the mass thereof. The produced impregnated substance (catalyst precursor) was dried overnight in the drier kept at 60° C., then the dried substance was calcined at 400° C. for 3 hours under an air flow, and a hydroisomerization catalyst E-A1 having a carbon content of 0.56% by mass was produced. The carbon content was measured with EMIA-920V manufactured by HORIBA, Ltd. by an in-oxygen airflow combustion-infrared ray absorption method.

Furthermore, the volume of micropores per unit mass of the prepared hydroisomerization catalyst was calculated in the following method. In order to remove moisture adsorbed by the hydroisomerization catalyst, pretreatment for evacuation at 150° C. for 5 hours was performed. For the pretreated hydroisomerization catalyst, nitrogen adsorption measurement was carried out with a BELSORP-max manufactured by BEL JAPAN, INC. at a liquid nitrogen temperature (−196° C.). The measured isothermal line of nitrogen adsorption was analyzed by a t-plot method, and the volume of micropores (cm$^3$/g) per unit mass of the hydroisomerization catalyst was determined.

Furthermore, the volume $V_Z$ of micropores per unit mass of the zeolite contained in the catalyst was calculated according to the following expression. Note that by carrying out the nitrogen adsorption measurement in the similar manner as that described above on alumina, which was used as the binder, it was observed that alumina included no micropores.

$$V_Z = V_c / M_z \times 100$$

where $V_c$ is a value of the volume of the micropores per unit mass of the hydroisomerization catalyst, and $M_z$ is the ratio of content (% by mass) of the zeolite contained in the catalyst.

Table 1 illustrates obtained results.

Example A-2

In a similar manner as Example A-1 except that the extruded body was heated at 350° C. for 3 hours under $N_2$ atmosphere and a support precursor was prepared, a hydroisomerization catalyst E-A2 having a carbon content of 0.47% by mass was produced.

Example A-3

In a similar manner as Example A-1 except that the extruded body was heated at 250° C. for 3 hours under $N_2$ atmosphere to prepare a support precursor, a hydroisomerization catalyst E-A3 having a carbon content of 0.70% by mass was produced.

Example A-4

In a similar manner as Example A-1 except that the catalyst precursor was heated at 380° C. for 3 hours in an air flow to produce a catalyst, a hydroisomerization catalyst E-A4 having a carbon content of 0.62% by mass was produced.

Example A-5

In a similar manner as Example A-1 except that the catalyst precursor was heated at 350° C. for 3 hours in an air flow to produce a catalyst, a hydroisomerization catalyst E-A5 having a carbon content of 0.81% by mass was produced.

Example A-6

In a similar manner as Example A-1 except that the extruded body was heated at 250° C. for 3 hours under $N_2$ atmosphere to prepare a support precursor and that the catalyst precursor was heated at 350° C. for 3 hours in an air flow to prepare a catalyst, a hydroisomerization catalyst E-A6 having a carbon content of 2.17% by mass was produced.

Example A-7

In a similar manner as Example A-1, a support precursor was prepared. Subsequently, a tetraamminepalladium nitrate $[Pd(NH_3)_4](NO_3)_2$ was dissolved in deionized water equivalent to a previously measured water absorption of the support precursor to prepare an impregnation solution. The solution was impregnated into the support precursor by an incipient wetness method, and supporting was performed so as to carry 0.3% by mass of palladium on the ZSM-22 zeolite in relation to the mass thereof. The produced impregnated substance (catalyst precursor) was dried overnight in the drier kept at 60° C., then the dried substance was calcined at 400° C. for 3 hours under an air flow, and a hydroisomerization catalyst E-A7 having a carbon content of 0.51% by mass was produced.

Example A-8

<Production of ZSM-48 Zeolite>

A ZSM-48 zeolite with the Si/Al ratio of 45 containing an organic template (hereinafter may be simply referred to as "ZSM-48") was synthesized on the basis of "Applied Catalysis A: General", vol. 299 (2006), pp. 167-174.

The following four types of reagents were prepared.
Reagent E: 2.97 g of sodium hydroxide
Reagent F: 0.80 g of aluminum sulfate octadecahydrate
Reagent G: 26.2 g of 1,6-hexanediamine (organic template)
Reagent H: 0.9 mL of 98% sulfuric acid solution
Reagent I: 75 g of aqueous solution ($SiO_2$ concentration: 40%) of colloidal silica (Ludox AS-40 manufactured by Grace Davison)

The reagents E through I were then added to 180 mg deionized water and the mixture was agitated at normal temperature for 2 hours until the reagents were completely dissolved therein.

The gelled substance prepared by the above-described operation was transferred into a stainless steel autoclave reactor having an internal volume of 100 mL, the autoclave reactor was rotated on a tumbling apparatus for 60 hours in an oven kept at 160° C. at the rotation speed of about 60 rpm to run a hydrothermal synthesis reaction. After the reaction was completely run, the reactor was cooled down, opened, and dried overnight in a drier kept at 60° C., and a ZSM-48 having the Si/Al ratio of 45 was produced.

<Ion Exchange of ZSM-48 Including Organic Templates>

An ion-exchanged $NH_4$-ZSM-48 was prepared by carrying out an operation similar to that performed in the ion exchange of ZSM-22 in Example A-1 except that a ZSM-48 containing an organic template and prepared in the above-described manner was used instead of the ZSM-22 containing an organic template.

A hydroisomerization catalyst E-A8 having a carbon content of 0.43% by mass was produced by producing an extruded body, heating the extruded body, preparing a catalyst precursor, and calcining the catalyst precursor by an operation similar to that in Example A-1 except that the $NH_4$-ZSM-48 produced in the above-described manner was used instead of the $NH_4$-ZSM-22.

Example A-9

<Production of SSZ-32 Zeolite>

An SSZ-32 zeolite (hereinafter may also be simply referred to as an "SSZ-32") was produced by hydrothermal synthesis in conformity with the method described in JP 2006-523136 A in the following manner.

Sodium hydroxides, aluminum sulfates, colloidal silica, isobutylamines, and N-methyl-N'-isopropyl-imidazolium cations were prepared by mixing at the following molar ratios:

$SiO_2/Al_2O_3=35$, and the total content of the isobutylamine and the N-methyl-N'-isopropyl-imidazolium cation was 0.2 times as large as the content of $SiO_2$.

The gelled substance prepared by the above-described operation was transferred into a stainless steel autoclave reactor having an internal volume of 100 mL, the autoclave reactor was rotated on a tumbling apparatus for 60 hours in an oven kept at 160° C. at the rotation speed of about 60 rpm to run a hydrothermal synthesis reaction. After the reaction was completely run, the reactor was cooled down, opened, and dried overnight in a drier kept at 60° C., and an SSZ-32 having the Si/Al ratio of 45 was produced.

<Ion Exchange of SSZ-32 Including Organic Templates>

An ion-exchanged $NH_4$-SSZ-32 was prepared by carrying out an operation similar to that performed in the ion exchange of ZSM-22 in Example A-1 except that an SSZ-32 containing an organic template and prepared in the above-described manner was used instead of the ZSM-22 containing an organic template.

A hydroisomerization catalyst E-A9 having a carbon content of 0.50% by mass was produced by producing an extruded body, heating the extruded body, preparing a catalyst precursor, and calcining the catalyst precursor by an operation similar to that in Example A-1 except that the $NH_4$-SSZ-32 produced in the above-described manner was used instead of the $NH_4$-ZSM-22.

Comparative Example A-1

In a similar manner as Example A-1 except that an extruded body was heated at 400° C. for 3 hours in an air flow to produce a support precursor, a hydroisomerization catalyst CE-A1 having a carbon content of 0.28% by mass was produced.

Comparative Example A-2

In a similar manner as Example A-1 except that an extruded body was heated at 400° C. for 3 hours under $N_2$ atmosphere to produce a support precursor, a hydroisomerization catalyst CE-A2 having a carbon content of 0.37% by mass was produced.

Comparative Example A-3

In a similar manner as Example A-1 except that an extruded body was heated at 450° C. for 3 hours under $N_2$ atmosphere to produce a support precursor, a hydroisomerization catalyst CE-A3 having a carbon content of 0.33% by mass was produced.

Comparative Example A-4

In a similar manner as Example A-1 except that a catalyst precursor was calcined at 300° C. for 3 hours in an air flow, a hydroisomerization catalyst CE-A4 having a carbon content of 2.68% by mass was produced.

Comparative Example A-5

In a similar manner as Example A-1 except that a catalyst precursor was calcined at 450° C. for 3 hours in an air flow, a hydroisomerization catalyst CE-A5 having a carbon content of 0.30% by mass was produced.

[Evaluation of Isomerization Selectivity of Catalyst]

For each catalyst produced in the above-described examples and comparative examples, the isomerization selectivity of the catalyst in the hydroisomerization reaction of hydrocarbons was evaluated by the following test. Note that in this test, normal hexadecane (nC16) was used as the hydrocarbon and the isomerization selectivity was evaluated by analyzing a reaction product of the hydroisomerization reaction run under the following conditions by means of the following reactor.

<Reactor>

As the reactor, an immobilized bed microreactor was prepared, which includes a 30 cm-long stainless steel tube with an inner diameter of 2.1 cm. The flow of gases, such as oxygen gas and hydrogen gas for activating the catalyst and nitrogen gas for purging, and normal hexadecane as a reaction raw material can be switched by a valve to be supplied to the microreactor. A 5 mg of catalyst was charged in a lowermost portion of the stainless steel tube and the reaction was run in the gas phase. Gaseous products of the reaction was sampled by a pressure-controlled sampling valve provided downstream of the microreactor; the sample was supplied to a gas chromatograph (GC) with a multi-capillary column and using a dimethylpolysiloxane stationary phase to be analyzed thereby.

<Reaction Condition>

The isomerization reaction of normal hexadecane was run under the following conditions in the presence of hydrogen:

Raw material (n-hexadecane): product of NACALAI TESQUE, INC. (purity: 99% or higher)

Reaction pressure: 0.20 MPa
Hydrogen/normal hexadecane ratio: 60 mol/mol
Reaction temperature: 280° C.

Note that in this test, in order to evaluate the relative merits of the catalysts for the isomerization selectivity, the space velocity was controlled to set the same conversion (95%) of normal hexadecane determined based on the following Expression (1):

Conversion of normal hexadecane ($nC16$) (% by mass)=[100−content of normal hexadecane in reaction product (% by mass)]     (1).

<Evaluation of Isomerization Selectivity>

The content of C16 isoparaffin in the reaction product (% by mass) was determined and the determined content was taken as the isomerization selectivity ratio (%) of the hydroisomerization catalyst. Table 1 illustrates the results.

TABLE 1

| Isomerization catalyst | Zeolite | Extruded body heating conditions | | Catalyst precursor calcining conditions | | Carbon content of catalyst (% by mass) | Volume of micropores per unit mass of catalyst (cm³/g) | Volume of micropores per unit mass of zeolite included in catalyst (cm³/g) | Active metal | Conversion of nC16 (%) | Isomerization selectivity (%) |
|---|---|---|---|---|---|---|---|---|---|---|---|
| | | Atmosphere | Temperature (° C.) | Atmosphere | Temperature (° C.) | | | | | | |
| Example A-1 | E-A1 | ZSM-22 | $N_2$ | 300 | Air | 400 | 0.56 | 0.055 | 0.079 | Pt | 95 | 93 |
| Example A-2 | E-A2 | ZSM-22 | $N_2$ | 350 | Air | 400 | 0.47 | 0.070 | 0.100 | Pt | 95 | 90 |
| Example A-3 | E-A3 | ZSM-22 | $N_2$ | 250 | Air | 400 | 0.70 | 0.045 | 0.064 | Pt | 95 | 85 |
| Example A-4 | E-A4 | ZSM-22 | $N_2$ | 350 | Air | 380 | 0.62 | 0.050 | 0.071 | Pt | 95 | 91 |
| Example A-5 | E-A5 | ZSM-22 | $N_2$ | 300 | Air | 350 | 0.81 | 0.039 | 0.056 | Pt | 95 | 88 |
| Example A-6 | E-A6 | ZSM-22 | $N_2$ | 250 | Air | 350 | 2.17 | 0.030 | 0.043 | Pt | 95 | 87 |
| Example A-7 | E-A7 | ZSM-22 | $N_2$ | 300 | Air | 400 | 0.51 | 0.061 | 0.087 | Pd | 95 | 90 |
| Example A-8 | E-A8 | ZSM-48 | $N_2$ | 300 | Air | 400 | 0.43 | 0.078 | 0.111 | Pt | 95 | 89 |
| Example A-9 | E-A9 | SSZ-32 | $N_2$ | 300 | Air | 400 | 0.50 | 0.062 | 0.089 | Pt | 95 | 87 |
| Comparative example A-1 | CE-A1 | ZSM-22 | Air | 400 | Air | 400 | 0.28 | 0.088 | 0.126 | Pt | 95 | 82 |
| Comparative example A-2 | CE-A2 | ZSM-22 | $N_2$ | 400 | Air | 400 | 0.37 | 0.085 | 0.121 | Pt | 95 | 83 |
| Comparative example A-3 | CE-A3 | ZSM-22 | $N_2$ | 450 | Air | 400 | 0.33 | 0.093 | 0.133 | Pt | 95 | 76 |
| Comparative example A-4 | CE-A4 | ZSM-22 | $N_2$ | 300 | Air | 300 | 2.68 | 0.021 | 0.030 | Pt | 95 | 82 |
| Comparative example A-5 | CE-A5 | ZSM-22 | $N_2$ | 300 | Air | 450 | 0.30 | 0.098 | 0.140 | Pt | 95 | 75 |

Examples A-10 Through A-18, Comparative Examples A-6 Through A-10

By using the catalysts produced in Examples A-1 through A-9 and Comparative Examples A-1 through A-5, dewaxing of waxes and separation/collection of lubricant base oil fractions were performed.

(Dewaxing of Wax)

100 mL of the extruded catalyst was charged into a stainless steel reaction tube having an inner diameter of 15 mm and a length of 380 mm, and a reduction treatment was carried out at a catalyst layer average temperature of 350° C. for 12 hours under a hydrogen flow (hydrogen partial pressure: 3 MPa). Then, a petroleum slack wax (distribution of the number of carbon atoms C10 to C40; the composition of this slack wax is illustrated in FIG. 1) was run, as a stock, at a reaction temperature of 315 to 340° C., a hydrogen partial pressure of 3 MPa, an LHSV of 1.0 h$^{-1}$, and a hydrogen/oil ratio of 500 NL/L, and then a dewaxing treatment by the hydroisomerization reaction was started. The reaction was run for 72 hours and reaction products were sampled and analyzed. Note that in FIG. 1, the letter "A" denotes the content of non-normal paraffins and the letter "B" denotes the content of normal paraffins.

Subsequently, the reaction temperature was raised in stages up to about 350° C. to increase the stock conversion with the hydrogen partial pressure, the LHSV, and the hydrogen/oil ratio unchanged. The reaction was run at respective reaction temperatures for 72 hours and when the reaction became stable, each reaction product was sampled and analyzed.

(Separation and Collection of Lubricant Base Oil Fractions)

On the basis of results of the analysis on each of the reaction products, each reaction product produced at a reaction temperature at which the conversion of normal paraffins was 100%, which is defined by the above-described Expression (I), fractionation was performed by the following operations and the following lubricant base oil fractions were separated and collected.

The reaction products produced at each reaction temperature at which the conversion of the normal paraffins was 100% was at first fractionated into a naphtha fraction, a kerosene and gas oil fraction, and heavy fraction. Furthermore, the heavy fraction was fractionated into a lubricant base oil fraction with a boiling point ranging from 330 to 410° C. and a kinetic viscosity of 2.7±0.1 mm$^2$/s at 100° C. (this fraction will be hereinafter referred to as a "lubricant base oil fraction 1"), and a lubricant base oil fraction with a boiling point ranging from 410 to 450° C. and a kinetic viscosity of 4.0±0.1 mm$^2$/s at 100° C. (this fraction will be hereinafter referred to as a "lubricant base oil fraction 2"). A lowest reaction temperature, at which the pour point of the lubricant base oil fraction 2 becomes −22.5° C. or lower and the viscosity index becomes 140 or greater, was taken as a reaction temperature Tc (° C.). Table 2 illustrates yields of the lubricant base oil fractions 1 and 2 at the reaction temperature Tc and properties of the lubricant base oil fraction 2.

in which the isomerization catalyst CE-A1 was used and the extruded body heating conditions of 400° C. and under air atmosphere were employed, and in Comparative Examples A-7 and A-8, in which the isomerization catalysts CE-A2 and CE-A3 were contacted, respectively, and the extruded body heating conditions of under N$_2$ atmosphere was employed but the heating temperature was 400° C. or higher. In addition, it was observed that the yields of lubricant base oil fraction 2 were below those of the examples in Comparative Example A-9, in which the isomerization catalyst CE-A4 was contacted and the catalyst precursor calcining conditions of 300° C. was employed, and in Comparative Example A-10, in which the isomerization catalysts CE-A5 was contacted and the catalyst precursor calcining condition of 450° C. was employed.

[Production of ZSM-22 Zeolite]

Preparation Example 1

At the start of the operation, the following four types of aqueous solutions were prepared.

Solution A: a solution prepared by dissolving 1.94 g of potassium hydroxide in 6.75 mL of deionized water.

Solution B: a solution prepared by dissolving 133 g of aluminum sulfate octadecahydrate in 5 mL of deionized water.

Solution C: a solution prepared by diluting 5.39 g of 1,8-diamino octane (an organic template; hereinafter simply referred to as "1,8-DAO") in 32.5 mL of deionized water.

Solution D: a solution prepared by diluting 18 g of colloidal silica (Ludox AS-40 manufactured by Grace Davison) in 31 ml of deionized water.

Then, the solution A was added to the solution B, and the mixture was agitated until aluminum components were completely dissolved. The solution C was added to the

TABLE 2

| | Isomerization catalyst | Reaction temperature Tc (° C.) | Yield of lubricant base oil fraction at reaction temperature Tc (%) | | Properties of lubricant base oil fraction 2 at reaction temperature Tc | |
|---|---|---|---|---|---|---|
| | | | Lubricant base oil fraction 1 | Lubricant base oil fraction 2 | Pour point (° C.) | Viscosity index |
| Example A-10 | E-A1 | 325 | 30 | 62 | −27.5 | 148 |
| Example A-11 | E-A2 | 325 | 31 | 58 | −27.5 | 147 |
| Example A-12 | E-A3 | 330 | 32 | 52 | −25.0 | 143 |
| Example A-13 | E-A4 | 325 | 32 | 54 | −27.5 | 147 |
| Example A-14 | E-A5 | 330 | 30 | 52 | −25.0 | 146 |
| Example A-15 | E-A6 | 340 | 31 | 50 | −27.5 | 146 |
| Example A-16 | E-A7 | 330 | 30 | 61 | −27.5 | 148 |
| Example A-17 | E-A8 | 320 | 34 | 57 | −25.0 | 145 |
| Example A-18 | E-A9 | 325 | 30 | 57 | −27.5 | 148 |
| Comparative example A-6 | CE-A1 | 320 | 31 | 48 | −27.5 | 146 |
| Comparative example A-7 | CE-A2 | 320 | 30 | 46 | −27.5 | 146 |
| Comparative example A-8 | CE-A3 | 320 | 42 | 39 | −27.5 | 140 |
| Comparative example A-9 | CE-A4 | 340 | 40 | 43 | −30.0 | 141 |
| Comparative example A-10 | CE-A5 | 320 | 44 | 38 | −27.5 | 139 |

It was observed that in Examples A-10 through A-18, in which the isomerization catalysts E-A1 through E-A9 were used, the lubricant base oil fraction 2 with a sufficiently low pour point and a sufficiently high viscosity index can be produced from a petroleum slack wax at a high yield. On the other hand, the yield of the lubricant base oil fraction 2 were below those of the examples in Comparative Example A-6, mixed solution, then the mixed solution containing the solutions A, B, and C was intensely agitated at room temperature and the agitated mixed solution was poured into the solution D. 0.25 g of powder of ZSM-22 zeolite (i.e., a zeolite thermally synthesized by using 1,6-diaminohexane as the organic template), which had been separately synthesized as a "seed crystal" for accelerating crystallization and which had not undergone any special treatment after the synthesis, was added to the mixed solution; and a gelled substance was prepared.

The gelled substance prepared by the above-described operation was transferred into a stainless steel autoclave reactor having an internal volume of 120 mL, the autoclave reactor was rotated on a tumbling apparatus for 60 hours in an oven kept at 150° C. at the rotation speed of about 60 rpm to run a hydrothermal synthesis reaction. After the reaction was completely run, the reactor was cooled down, opened, and dried overnight in a drier kept at 60° C., and as a result, a ZSM-22 having the Si/Al ratio of 45 was produced.

<Ion Exchange of ZSM-22 Zeolite Including Organic Templates>

An ion-exchanging treatment was carried out for the ZSM-22 zeolite produced in the above-described manner in an aqueous solution containing ammonium ions by the following operations.

The ZSM-22 zeolite produced in the above-described manner was transferred into a flask, then 100 mL of 0.5 N-ammonium chloride aqueous solution for 1 g of ZSM-22 zeolite was added, and the mixture was heated under flux for 6 hours. Then the mixture was cooled down to room temperature, the supernatant liquid was removed, and the crystalline aluminosilicate was washed in the deionized water. The same amount of a 0.5 N-ammonium chloride aqueous solution as that described above was added to the mixture again, and the mixture was heated under reflux for 12 hours.

Subsequently, solid contents were extracted by filtration, the extracted solid contents were then washed with the deionized water, dried overnight in a drier kept at 60° C., and an ion-exchanged $NH_4$-ZSM-22 zeolite was produced (this ZSM-22 zeolite will hereafter be referred to as "$NH_4$-ZSM-22 zeolite (1,8-DAO)"). The ZSM-22 zeolite was ion-exchanged in a state in which 1,8-DAO, which is an organic template, were contained, Comparative Preparation Example 1

In a similar manner as Preparation Example 1 except that an aqueous solution containing 4.18 g of 1,6-hexanediamine (i.e., an organic template; hereinafter simply referred to as "1,6-DAH") diluted in 32.5 mL deionized water was used as the solution C, an ion-exchanged $NH_4$-ZSM-22 zeolite was produced (hereinafter referred to as an "$NH_4$-ZSM-22 zeolite (1,6-DAH)").

<Powder X-ray Diffraction Pattern, Measurement of External Surface Area and Volume of Micropores>

The $NH_4$-ZSM-22 zeolite (1,8-DAO) and $NH_4$-ZSM-22 zeolite (1,6-DAH) produced by the above-described operations were dried at 60° C. and calcined under the same conditions as the extruded body calcining conditions shown in Table 5, respectively, and calcined powders were produced. For the produced calcined powder, the powder X-ray diffraction patterns, the external surface areas, and the volumes of micropores were measured in the following manner.

[Powder X-Ray Diffraction Pattern]

The X-ray diffraction measurement of calcined powders of zeolite was performed with "X-ray Diffractometer RINT 2500" (a product of Rigaku Corporation) under the following conditions:

X-ray source: Cu-Kα line;
Voltage: 50 kV; and
Current: 200 mA

Figure 2:
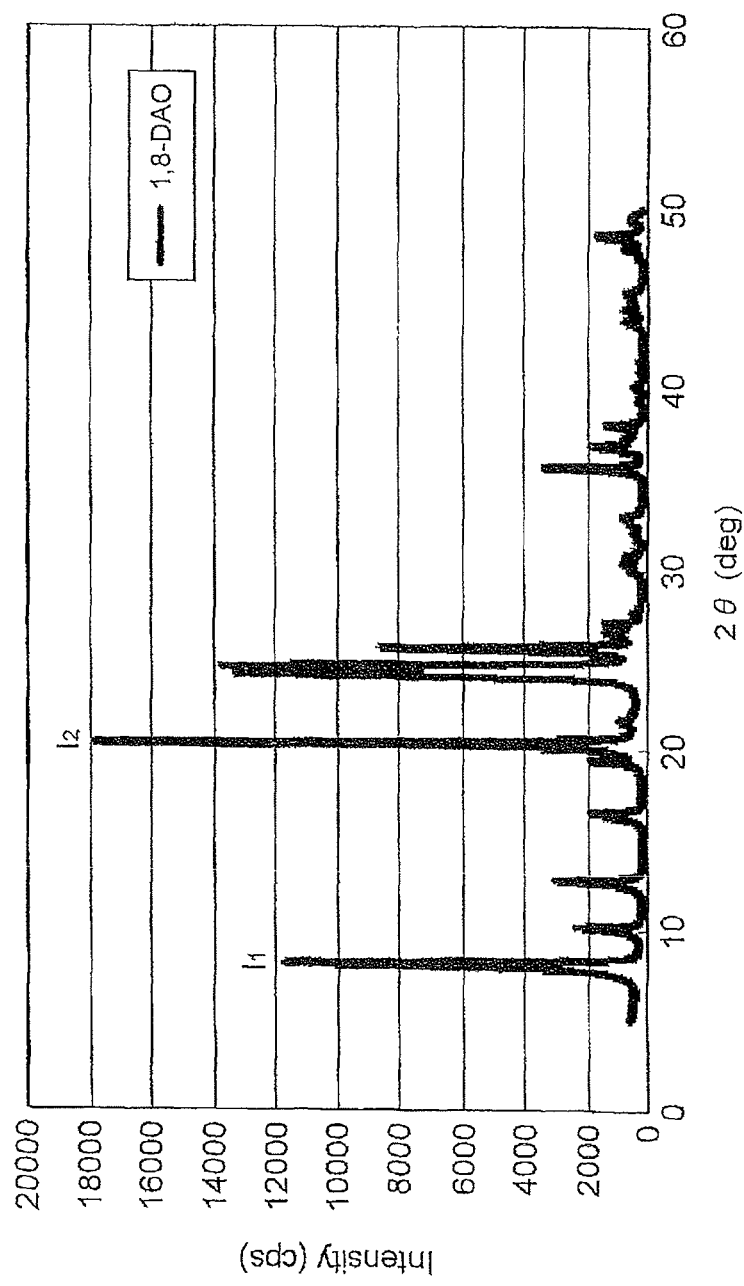
FIG. 2 illustrates powder X-ray diffraction patterns of calcined powders of an NH$_4$-ZSM-22 zeolite (1,8-DAO)
Figure 3:
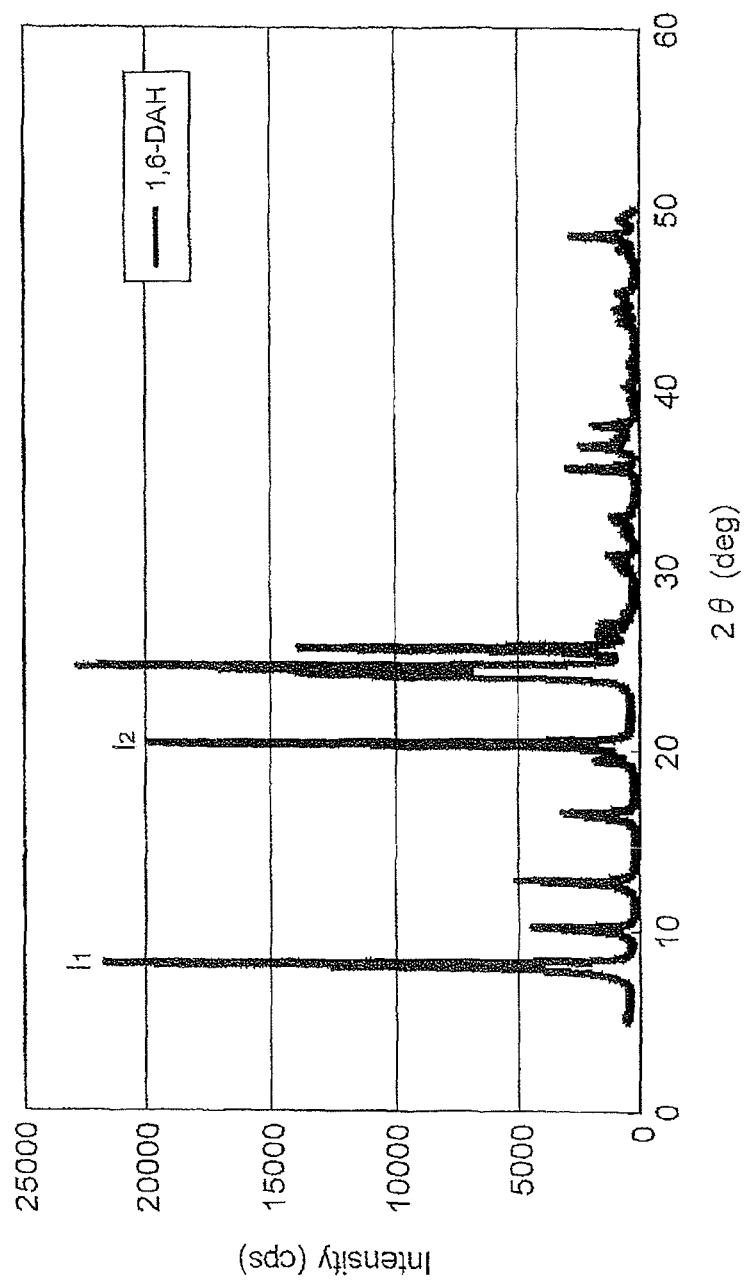
FIG. 3 illustrates powder X-ray diffraction patterns of calcined powders of an NH$_4$-ZSM-22 zeolite (1,6-DAH).

FIGS. 2 and 3 illustrate the observed powder X-ray diffraction patterns. FIG. 2 illustrates a powder X-ray diffraction pattern of calcined powder of the $NH_4$-ZSM-22 zeolite (1,8-DAO) and FIG. 3 illustrates a powder X-ray diffraction pattern of calcined powder of the $NH_4$-ZSM-22 zeolite (1,6-DAB).

In the powder X-ray diffraction pattern of the calcined powder of the $NH_4$-ZSM-22 zeolite (1,8-DAO), the intensity ratio $I_1/I_2$ between the peak intensity $I_1$ appearing at $2\theta=8.1\pm0.5°$ and the peak intensity $I_2$ appearing at $2\theta=20.3\pm0.5°$ was 0.62. On the other hand, in the powder X-ray diffraction pattern of the calcined powder of the $NH_4$-ZSM-22 zeolite (1,6-DAH), the intensity ratio $I_1/I_2$ was 1.15.

TABLE 3

| | Intensity, cps | | |
|---|---|---|---|
| | $I_1$ $2\theta = 8.12°$ | $I_2$ $2\theta = 20.34°$ | $I_1/I_2$ |
| Calcined powder of the $NH_4$—ZSM-22 zeolite (1,8-DAO) | 10970.8 | 17698.3 | 0.62 |
| Calcined powder of the $NH_4$—ZSM-22 zeolite (1,6-DAH) | 21693.3 | 18880.8 | 1.15 |

In the powder X-ray diffraction pattern of the zeolite, a peak appearing at $2\theta=8.1°$ represents a crystal of a (110) plane and a peak appearing at $2\theta=20.3°$ represents a crystal of a (021) plane. In a ZSM-22 zeolite, the (110) plane is considered to be an index indicating the crystallizability in the major axis (L), and the (021) plane is considered to be an index indicating the crystallizability in the minor axis (D). The intensity ratio $I_1/I_2$ for the $NH_4$-ZSM-22 zeolite (1,8-DAO) was 0.62; a value smaller than 1.15 for the $NH_4$-ZSM-22 zeolite (1,6-DAH) showing that the $NH_4$-ZSM-22 zeolite (1,8-DAO) constituted a microcrystal.

[External Surface Area and Volume of Micropores]

At first, in order to remove moisture adsorbed by the calcined powder of the zeolite, a pretreatment for evacuation at 150° C. for 5 hours was performed. For the pretreated calcined powder, nitrogen adsorption measurement was carried out with a BELSORP-max manufactured by BEL JAPAN, INC. at a liquid nitrogen temperature (−196° C.). The measured isothermal line of nitrogen adsorption was analyzed by a t-plot method, and the volume of micropores ($cm^3/g$) per unit mass of the calcined powder was determined. Table 4 illustrates the obtained results.

TABLE 4

| | External surface area ($m^2/g$) | Volume of micropores ($cm^3/g$) |
|---|---|---|
| Calcined powder of the $NH_4$—ZSM-22 zeolite (1,8-DAO) | 90 | 0.04 |
| Calcined powder of the $NH_4$—ZSM-22 zeolite (1,6-DAH) | 23 | 0.079 |

[Production of Hydroisomerization Catalyst]

Example B-1

<Mixing of Binder, Extruding, Calcination>

The $NH_4$-ZSM-22 (1,8-DAO) produced by the above-described operation and alumina, which was used as a binder, were mixed at the mass ratio of 7:3, then a small amount of deionized water was added to the mixture, and then the mixture was kneaded. The produced viscous fluid was charged into an extruder to be extruded, and a cylindrical extruded body having the diameter of about 1.6 mm and the length of about 10 mm was prepared. This extruded body was heated at 300° C. for 3 hours under $N_2$ atmosphere, and a support precursor was produced.

<Supporting of Platinum, Calcination>

A tetraammineplatinum dinitrate $[Pt(NH_3)_4](NO_3)_2$ was dissolved in deionized water equivalent to a previously measured water absorption of the support precursor, and an impregnation solution was prepared. The solution was impregnated into the support precursor by an incipient wetness method, and supporting was performed so as to allow 0.3% by mass of platinum to be supported on the ZSM-22 zeolite in relation to the mass thereof. The produced impregnated substance (catalyst precursor) was dried overnight in the drier kept at 60° C., then the dried substance was calcined at 400° C. for 3 hours under an air flow, and a hydroisomerization catalyst E-B1 having a carbon content of 1.50% by mass was produced. The carbon content was measured with BMA-920V manufactured by HORIBA, Ltd. by an in-oxygen airflow combustion-infrared ray absorption method.

Example B-2

In a similar manner as Example B-1 except that the extruded body was heated at 350° C. for 3 hours under air atmosphere and a support precursor was prepared, a hydroisomerization catalyst E-B2 having a carbon content of 2.21% by mass was produced.

Example B-3

In a similar manner as Example B-1 except that the extruded body was heated at 250° C. for 3 hours under $N_2$ atmosphere and a support precursor was prepared, a hydroisomerization catalyst E-B3 having a carbon content of 1.47% by mass was produced.

Example B-4

In a similar manner as Example B-1 except that the catalyst precursor was heated at 380° C. for 3 hours under air atmosphere and a catalyst was prepared, a hydroisomerization catalyst E-B4 having a carbon content of 0.89% by mass was produced.

Example B-5

In a similar manner as Example B-1, a support precursor was prepared. Subsequently, a tetraamminepalladium nitrate $[Pd(NH_3)_4](NO_3)_2$ was dissolved in deionized water equivalent to a previously measured water absorption of the support precursor to prepare an impregnation solution. The solution was impregnated into the support precursor by an incipient wetness method, and supporting was performed so as to carry 0.3% by mass of palladium on the ZSM-22 zeolite in relation to the mass thereof. The produced impregnated substance (catalyst precursor) was dried overnight in the drier kept at 60° C., then the dried substance was calcined at 400° C. for 3 hours under an air flow, and a hydroisomerization catalyst E-B5 having a carbon content of 1.42% by mass was produced.

Reference Example B-1

In a similar manner as Example B-1 except that the $NH_4$-ZSM-22 zeolite (1,6-DAH) as used instead of the $NH_4$-ZSM-22 zeolite (1,8-DAO), a hydroisomerization catalyst CE-B1 having a carbon content of 0.56% by mass was produced.

Reference Example B-2

In a similar manner as Example B-1 except that the extruded body was heated at 550° C. for 3 hours and a support precursor was prepared, a hydroisomerization catalyst CE-B2 having a carbon content of 0.35% by mass was produced.

Comparative Example B-3

<Synthesis of ZSM-22 Zeolite>

A ZSM-22 zeolite including a crystalline aluminosilicate having the Si/Al ratio of 36 was produced by hydrothermal synthesis in the following manner. As reagents, colloidal silica (Ludox AS-30 produced by Sigma-Aldrich Co. LLC.), aluminum sulfate octadecahydrate (produced by Wako Pure Chemical Industries, Ltd.), potassium hydroxide (produced by Wako Pure Chemical Industries, Ltd.), 1,8-diamino octane (structure directing agent (SDA) produced by Sigma-Aldrich Co. LLC.) were mixed at the following molar ratio, and a gelled substance was prepared:

$SiO_2:SDA:KOH:Al:H_2O=1.0:0.3:0.3:0.022:40$.

The gelled substance prepared by the above-described operation was transferred into a stainless steel autoclave reactor having an internal volume of 120 mL, the autoclave reactor was rotated on a tumbling apparatus for 72 hours in an oven kept at 160° C. at the rotation speed of 20 rpm to run a hydrothermal synthesis reaction. After the hydrothermal synthesis reaction was completed, the reactor was cooled down, the produced solid contents were extracted from each reactor by filtration, the extracted solid contents were then washed with deionized water, dried overnight in a drier kept at 80° C., then the dried substance was calcined at 650° C. for 10 hours, and thus a ZSM-22 zeolite having the Si/Al ratio of 36 was produced.

<Production of Ion-Exchanged ZSM-22>

The ZSM-22 zeolite produced in the above-described manner was transferred into a flask, then was mixed at the molar ratio of ZSM-22 zeolite:$NH_4NO_3$:$H_2O$=1:2:50, the ion exchange was performed at 80° C. for 24 hours, and this operation was repeated three times. Then solid contents were extracted by filtration, the extracted solid contents were then washed with deionized water, dried overnight in a drier kept at 80° C., and thus an ion-exchanged $NH_4$-ZSM-22 zeolite was produced.

<Mixing of Binder, Extruding, Calcination>

The $NH_4$-ZSM-22 zeolite produced by the above-described operation and alumina, which was used as a binder, was mixed at the mass ratio of 7:3, then a small amount of deionized water was added to the mixture, and then the mixture was kneaded. The produced viscous fluid was charged into an extruder to be extruded, and a cylindrical extruded body having the diameter of about 1.5 mm and the length of about 5 mm was prepared. This extruded body was dried for 3 hours in a drier kept at 120° C. under air flow, was then calcined at 550° C. for 3 hours under air flow, and thus extruded and calcined support particles were produced.

<Supporting of Platinum, Calcination>

A tetraammine dichloroplatinum (II) $(Pt(NH_3)_4Cl_2)$ was dissolved in deionized water equivalent to a previously measured water absorption of the extruded and calcined support particles, and an impregnation solution was prepared. The solution was impregnated into the extruded and calcined support particles by an incipient wetness method, and supporting was performed so as to allow 0.5% by mass of platinum to be supported on the ZSM-22 zeolite in relation to the mass thereof. The produced impregnated substance was dried overnight in a drier kept at 60° C., then the dried substance was calcined at 550° C. for 3 hours under an air flow, and a hydroisomerization catalyst CE-B3 having a carbon content of 0.30% by mass was produced.

[Volume of Micropores per Unit Mass of Hydroisomerization Catalyst]

The volume of micropores per unit mass of the hydroisomerization catalyst produced by the above-described operation was determined by the following method. In order to remove moisture adsorbed by the hydroisomerization catalyst, pretreatment for evacuation at 150° C. for 5 hours was performed. For the pretreated hydroisomerization catalyst, nitrogen adsorption measurement was carried out with a BELSORP-max manufactured by BEL JAPAN, INC. at a liquid nitrogen temperature (−196° C.). The measured isothermal line of nitrogen adsorption was analyzed by a t-plot method, and the volume of micropores ($cm^3/g$) per unit mass of the hydroisomerization catalyst was determined.

[Volume of Micropores per Unit Mass of Zeolite Included in Catalyst]

A zeolite used for preparing a catalyst was heated and calcined under the same condition as that for calcining an extruded body in preparing a catalyst. For the calcined powder produced in this manner, nitrogen adsorption measurement was carried out with a BELSORP-max manufactured by BEL JAPAN, INC. at a liquid nitrogen temperature (−196° C.). The measured isothermal line of nitrogen adsorption was analyzed by a t-plot method, and the volume of micropores per unit mass of the catalyst ($cm^3/g$) was determined, and the determined volume was taken as the volume of micropores per unit mass of the zeolite included in the catalyst.

[Evaluation of Isomerization Selectivity of Catalyst]

For each catalyst produced in the above-described examples and comparative examples, the isomerization selectivity of the catalyst in the hydroisomerization reaction of hydrocarbons was evaluated by the following test. Note that in this test, normal hexadecane (nC16) was used as the hydrocarbon and the isomerization selectivity was evaluated by analyzing a reaction product of the hydroisomerization reaction run under the following conditions by means of the following reactor.

<Reactor>

As the reactor, an immobilized bed microreactor was prepared, which includes a 30 cm-long stainless steel tube with an inner diameter of 2.1 cm. The flow of gases, such as oxygen gas and hydrogen gas for activating the catalyst and nitrogen gas for purging, and normal hexadecane as a reaction raw material can be switched by a valve to be supplied to the microreactor. A 5 mg of catalyst was charged in a lowermost portion of the stainless steel tube and the reaction was run in the gas phase. Gaseous products of the reaction was sampled by a pressure-controlled sampling valve provided downstream of the microreactor; the sample was supplied to a gas chromatograph (GC) with a multi-capillary column and using a dimethylpolysiloxane stationary phase to be analyzed thereby.

<Reaction Condition>

The isomerization reaction of normal hexadecane was run under the following conditions in the presence of hydrogen:

Raw material (n-hexadecane): product of NACALAI TESQUE, INC. (purity: 99% or higher)

Reaction pressure: 0.20 MPa

Hydrogen/normal hexadecane ratio: 60 mol/mol

Reaction temperature: 320° C.

Note that in order to verify whether the catalyst was capable of inhibiting the cracking reaction at a high level, the reaction was run at a high temperature, at which the cracking reaction may easily develop.

Note that in this test, in order to evaluate the relative merits of the catalysts for the isomerization selectivity, the space velocity was controlled to set the same conversion (95%) of normal hexadecane determined based on the following Expression (1):

Conversion of normal hexadecane (nC16) (% by mass)=[100−content of normal hexadecane in reaction product (% by mass)]  (1).

<Evaluation of Isomerization Selectivity>

The content of C16 isoparaffin in the reaction product (% by mass) was determined and the determined content was taken as the isomerization selectivity ratio (%) of the hydroisomerization catalyst. Table 5 illustrates the results.

TABLE 5

| | Isomerization catalyst | Template | Zeolite external surface area ($m^3/g$) | Extruded body calcining conditions Atmosphere | Extruded body calcining conditions Temperature (° C.) | Catalyst precursor calcining condition Temperature (° C.) | Carbon content of catalyst (% by mass) | Volume of micropores per unit mass of catalyst ($cm^3/g$) | Volume of micropores per unit mass of zeolite included in catalyst ($cm^3/g$) | Active metal | Conversion of nC16 (%) | Isomerization selectivity (%) |
|---|---|---|---|---|---|---|---|---|---|---|---|---|
| Example B-1 | E-B1 | 1,8-DAO | 90 | $N_2$ | 300 | 400 | 1.50 | 0.028 | 0.04 | Pt | 95 | 75 |
| Example B-2 | E-B2 | 1,8-DAO | 89 | Air | 350 | 400 | 2.21 | 0.014 | 0.02 | Pt | 95 | 78 |
| Example B-3 | E-B3 | 1,8-DAO | 90 | $N_2$ | 250 | 400 | 1.47 | 0.028 | 0.04 | Pt | 95 | 74 |
| Example B-4 | E-B4 | 1,8-DAO | 90 | $N_2$ | 300 | 380 | 0.89 | 0.035 | 0.05 | Pt | 95 | 72 |
| Example B-5 | E-B5 | 1,8-DAO | 90 | $N_2$ | 300 | 400 | 1.42 | 0.028 | 0.04 | Pd | 95 | 75 |
| Reference Example B-1 | CE-B1 | 1,6-DAH | 23 | $N_2$ | 300 | 400 | 0.56 | 0.055 | 0.079 | Pt | 95 | 51 |
| Comparative example B-2 | CE-B2 | 1,8-DAO | 39 | Air | 550 | 400 | 0.35 | 0.098 | 0.14 | Pt | 95 | 63 |
| Comparative example B-3 | CE-B3 | 1,8-DAO | 15 | Air | 650 | 550 | 0.30 | 0.124 | 0.18 | Pt | 95 | 39 |

Examples B-6 Through B-10, Reference Example B-4, Comparative Examples B-5 and B-6

By using the catalysts produced in Examples B-1 through B-5, Reference Example B-1, and Comparative Examples B-2 and B-3, dewaxing of waxes and separation/collection of lubricant base oil fractions were performed.

(Dewaxing of Wax)

100 mL of the extruded catalyst was charged into a stainless steel reaction tube having an inner diameter of 15 mm and a length of 380 mm, and a reduction treatment was carried out at a catalyst layer average temperature of 350° C. for 12 hours under a hydrogen flow (hydrogen partial pressure: 3 MPa). Then, a petroleum slack wax (distribution of the number of carbon atoms C10 to C40; the composition of this slack wax is illustrated in Table 6) was run, as a stock, at a reaction temperature of 315 to 340° C., a hydrogen partial pressure of 3 MPa, an LHSV of 1.0 h$^{-1}$, and a hydrogen/oil ratio of 500 NL/L, and then a dewaxing treatment by the hydroisomerization reaction was started. The reaction was run for 72 hours and reaction products were sampled and analyzed.

TABLE 6

| Number of carbon atoms | Content of non-normal paraffin (% by mass) | Content of normal paraffin (% by mass) | Total content (% by mass) |
| --- | --- | --- | --- |
| C18 | | | 0.00 |
| C19 | | 0.10 | 0.10 |
| C20 | | 0.20 | 0.20 |
| C21 | | 0.30 | 0.30 |
| C22 | | 0.40 | 0.40 |
| C23 | 0.10 | 0.60 | 0.70 |
| C24 | 0.20 | 0.80 | 1.00 |
| C25 | 0.50 | 1.00 | 1.50 |
| C26 | 1.00 | 1.50 | 2.50 |
| C27 | 1.60 | 2.00 | 3.60 |
| C28 | 2.90 | 2.80 | 5.70 |
| C29 | 4.90 | 3.50 | 8.40 |
| C30 | 7.70 | 4.10 | 11.80 |
| C31 | 9.80 | 4.70 | 14.50 |
| C32 | 10.60 | 4.30 | 14.90 |
| C33 | 9.30 | 3.00 | 12.30 |
| C34 | 6.80 | 1.80 | 8.60 |
| C35 | 4.40 | 1.20 | 5.60 |
| C36 | 2.80 | 0.60 | 3.40 |
| C37 | 1.50 | 0.30 | 1.80 |
| C38 | 0.90 | 0.20 | 1.10 |
| C39 | 0.60 | 0.10 | 0.70 |
| C40 | 0.40 | | 0.40 |

TABLE 6-continued

| Number of carbon atoms | Content of non-normal paraffin (% by mass) | Content of normal paraffin (% by mass) | Total content (% by mass) |
| --- | --- | --- | --- |
| C41 | 0.20 | | 0.20 |
| C42 | 0.10 | | 0.10 |
| C43 | 0.10 | | 0.10 |
| C44 | 0.10 | | 0.10 |
| Total content (% by mass) | 66.50 | 33.50 | 100.00 |

Subsequently, the reaction temperature was raised in stages up to about 350° C. to increase the stock conversion with the hydrogen partial pressure, the LHSV, and the hydrogen/oil ratio unchanged. The reaction was run for 72 hours at respective reaction temperatures and when the reaction became stable, each reaction product was sampled and analyzed.

(Separation and Collection of Lubricant Base Oil Fractions)

On the basis of results of the analysis on each of the reaction products, each reaction product produced at a reaction temperature at which the conversion of normal paraffins was 100%, which is defined by the above-described Expression (I), fractionation was performed by the following operations and the following lubricant base oil fractions were separated and collected.

The reaction products produced at each reaction temperature at which the conversion of the normal paraffins was 100% was at first fractionated into a naphtha fraction, a kerosene and gas oil fraction, and heavy fraction. Furthermore, the heavy fraction was fractionated into a lubricant base oil fraction with a boiling point ranging from 330 to 410° C. and a kinetic viscosity of 2.7±0.1 mm$^2$/s at 100° C. (this fraction will be hereinafter referred to as a "lubricant base oil fraction 1"), and a lubricant base oil fraction with a boiling point ranging from 410 to 450° C. and a kinetic viscosity of 4.0±0.1 mm$^2$/s at 100° C. (this fraction will be hereinafter referred to as a "lubricant base oil fraction 2"). A lowest reaction temperature, at which the pour point of the lubricant base oil fraction 2 becomes −22.5° C. or lower and the viscosity index becomes 140 or greater, was taken as a reaction temperature Tc (° C.). Table 7 illustrates the weight of C1 through C4 included in the naphtha, the total yield of the lubricant base oil fractions 1 and 2 at the reaction temperature Tc, and properties of the lubricant base oil fraction 2.

TABLE 7

| | Isomerization catalyst | Reaction temperature Tc (° C.) | Yield of C1 through C4 included in naphtha at reaction temperature Tc (%) | Total yield of lubricant base oil fractions 1 and 2 at reaction temperature Tc (%) | Properties of lubricant base oil fraction 2 at reaction temperature Tc | |
| --- | --- | --- | --- | --- | --- | --- |
| | | | | | Pour point (° C.) | Viscosity index |
| Example B-6 | E-B1 | 325 | 4 | 85 | −22.5 | 142 |
| Example B-7 | E-B2 | 325 | 4 | 86 | −22.5 | 143 |
| Example B-8 | E-B3 | 325 | 3 | 86 | −22.5 | 143 |
| Example B-9 | E-B4 | 325 | 4 | 85 | −22.5 | 143 |
| Example B-10 | E-B5 | 330 | 4 | 82 | −22.5 | 142 |
| Reference example B-4 | CE-B1 | 325 | 6 | 78 | −22.5 | 141 |
| Comparative example B-5 | CE-B2 | 325 | 8 | 76 | −22.5 | 140 |
| Comparative example B-6 | CE-B3 | 325 | 10 | 73 | −22.5 | 138 |

It was observed that in Examples B-6 through B10, in which the isomerization catalysts E-B1 through E-B5 were used, the lubricant base oil fractions 1 and 2 can be produced from a petroleum slack wax at a high yield. On the other hand, the total yield of the lubricant base oil fractions 1 and 2 was below the total yields of Examples B-6 through B-10 in Reference Example B-4, in which the isomerization catalyst CE-B1 prepared by contacting with the $NH_4$-ZSM-22 zeolite (1,6-DAB) synthesized by using 1,6-diamino hexane, Comparative Example B-5, in which the isomerization catalyst CE-B2 prepared under extruded body heating condition of 550° C., which temperature exceeding 350° C., was set, and Comparative Example B-6, in which the isomerization catalyst CE-B3 prepared by contacting with the zeolite produced by undergoing ion exchange in a state in which no template was contained.

Examples B-11 and B-12, Reference Example B-7, and Comparative Example B-8

By using the catalysts produced in Examples B-1 and B-2, Reference Example B-1, and Comparative Example B-3, dewaxing of waxes and separation/collection of lubricant base oil fractions were performed.

(Dewaxing of Wax)

100 mL of the extruded catalyst was charged into a stainless steel reaction tube having an inner diameter of 15 mm and a length of 380 mm, and a reduction treatment was carried out at a catalyst layer average temperature of 350° C. for 12 hours under a hydrogen flow (hydrogen partial pressure: 3 MPa). On the other hand, a part of aromatic hydrocarbon of a vacuum gas oil produced by treating an Arabian light crude, as a stock, was extracted by an extraction tower in furfural and eliminated. Subsequently, the hydrocarbon oil produced by the operation (sulfur contents in the treated oil: 8,175 mass ppm; aromatic component: 27.8% by mass) was hydrotreated by contacting the same with a cobalt-molybdenum hydrogenation catalyst at the hydrogen partial pressure of 11.1 MPa, the reaction temperature of 330° C., and the LHSV of 1 $h^{-1}$ to control the level of the sulfur contents at about 20 mass ppm, and the hydrocarbon oil produced thereby (distribution of the number of carbon atoms C17 to C37; aromatic component: 21.2% by mass; sulfur component: 21.2 mass ppm; Table 8 illustrates its composition) was run under the following conditions: reaction temperature: 290 to 350° C.; hydrogen partial pressure: 11.1 MPa; LHSV: 1 $h^{-1}$; hydrogen/oil ratio: 500 NL/L, and the dewaxing treatment by the hydrogenation isomerization reaction was started. The reaction was run for 72 hours and reaction products were sampled and analyzed.

TABLE 8

| Number of carbon atoms | Content of non-normal paraffin (% by mass) | Content of normal paraffin (% by mass) | Total content (% by mass) |
| --- | --- | --- | --- |
| C16 | | | 0.00 |
| C17 | 0.01 | | 0.01 |
| C18 | 0.04 | 0.01 | 0.05 |
| C19 | 0.09 | 0.02 | 0.11 |
| C20 | 0.23 | 0.04 | 0.27 |
| C21 | 0.48 | 0.12 | 0.60 |
| C22 | 1.06 | 0.25 | 1.31 |
| C23 | 2.13 | 0.49 | 2.62 |
| C24 | 4.20 | 0.86 | 5.06 |
| C25 | 6.89 | 1.24 | 8.13 |
| C26 | 10.20 | 1.49 | 11.69 |

TABLE 8-continued

| Number of carbon atoms | Content of non-normal paraffin (% by mass) | Content of normal paraffin (% by mass) | Total content (% by mass) |
| --- | --- | --- | --- |
| C27 | 13.17 | 1.41 | 14.58 |
| C28 | 15.17 | 1.34 | 16.51 |
| C29 | 13.91 | 0.99 | 14.90 |
| C30 | 11.13 | 0.63 | 11.76 |
| C31 | 6.82 | 0.33 | 7.15 |
| C32 | 3.31 | 0.14 | 3.45 |
| C33 | 1.21 | 0.04 | 1.25 |
| C34 | 0.40 | 0.01 | 0.41 |
| C35 | 0.10 | | 0.10 |
| C36 | 0.03 | | 0.03 |
| C37 | 0.01 | | 0.01 |
| Total content (% by mass) | 90.59 | 9.41 | 100.00 |

Subsequently, the reaction temperature was raised in stages up to about 340° C. to increase the stock conversion with the hydrogen partial pressure, the LHSV, and the hydrogen/oil ratio unchanged. The reaction was run for 12 hours at respective reaction temperatures and when the reaction became stable, each reaction product was sampled and analyzed.

(Separation and Collection of Lubricant Base Oil Fractions)

On the basis of results of the analysis on each of the reaction products, each reaction product produced at a reaction temperature at which the conversion of normal paraffins was 100%, which is defined by the above-described Expression (I), fractionation was performed by the following operations and the following lubricant base oil fractions were separated and collected.

The reaction products produced at each reaction temperature at which the conversion of the normal paraffins was 100% was at first fractionated into a naphtha fraction, a kerosene and gas oil fraction, and heavy fraction. Furthermore, the heavy fraction was fractionated into a lubricant base oil fraction with a boiling point ranging from 330 to 460° C. and a kinetic viscosity of 2.7±0.1 $mm^2/s$ at 100° C. (this fraction will be hereinafter referred to as a "lubricant base oil fraction 3"), and a lubricant base oil fraction with a boiling point ranging from 460 to 530° C. and a kinetic viscosity of 4.9±0.1 $mm^2/s$ at 100° C. (this fraction will be hereinafter referred to as a "lubricant base oil fraction 4"). A lowest reaction temperature, at which the pour point of the lubricant base oil fraction 4 becomes −12.5° C. or lower and the viscosity index becomes 100 or greater, was taken as a reaction temperature Tc (° C.). Table 9 illustrates the weight of C1 through C4 included in the naphtha, the total yield of the lubricant base oil fractions 3 and 4 at the reaction temperature Tc, and properties of the lubricant base oil fraction 4.

TABLE 9

|  | Isomerization catalyst | Reaction temperature Tc (° C.) | Yield of C1 through C4 included in naphtha at reaction temperature Tc (%) | Total yield of lubricant base oil fractions 3 and 4 at reaction temperature Tc (%) | Properties of lubricant base oil fraction 4 at reaction temperature Tc | |
| --- | --- | --- | --- | --- | --- | --- |
|  |  |  |  |  | Pour point (° C.) | Viscosity index |
| Example B-11 | E-B1 | 300 | 0.8 | 97.1 | −12.5 | 106 |
| Example B-12 | E-B2 | 300 | 0.6 | 97.7 | −12.5 | 106 |
| Reference example B-7 | CE-B1 | 300 | 3.1 | 94.8 | −12.5 | 105 |
| Comparative example 13-8 | CE-B3 | 300 | 6.4 | 91.1 | −12.5 | 103 |

It was observed that in Examples B-11 and B12, in which the isomerization catalysts E-B1 and E-B2 were used, the lubricant base oil fractions 3 and 4 can be produced from a hydrocarbon oil produced by extracting a part of aromatic hydrocarbon of the vacuum gas oil by the extraction tower in furfural. On the other hand, the total yield of the lubricant base oil fractions 3 and 4 was below the total yields of Examples B-11 and B-12 in Reference Example B-7, in which the isomerization catalyst CE-B1 prepared by contacting with the NH$_4$-ZSM-22 zeolite (1,6-DAH) synthesized by using 1,6-diamino hexane, and Comparative Example B-8, in which the isomerization catalyst CE-B3 prepared by contacting with the zeolite produced by undergoing ion exchange in a state in which no template was contained.

The invention claimed is:

1. A method for dewaxing hydrocarbon oil comprising:
contacting a hydrocarbon oil comprising normal paraffins having 10 or more carbon atoms with a hydroisomerization catalyst in the presence of hydrogen to convert some or all of the normal paraffins into isoparaffins,
wherein the hydroisomerization catalyst is produced by a process comprising:
a first step of preparing a support precursor by heating a mixture containing an ion-exchanged zeolite and a binder, the ion-exchanged zeolite being prepared by ion-exchanging an organic template-containing zeolite which contains an organic template and has a one-dimensional pore structure including a 10-membered ring in a solution containing ammonium ions and/or protons, at a temperature of 250 to 350° C. under N$_2$ atmosphere, and
a second step of preparing a hydroisomerization catalyst, which is prepared by calcining a catalyst precursor, the catalyst precursor being prepared based on the support precursor containing a platinum salt and/or a palladium salt, at a temperature of 350 to 400° C. in an atmosphere containing molecular oxygen, the hydroisomerization catalyst containing a support which includes a zeolite and carries platinum and/or palladium;
and wherein the organic template contains 1,8-diamino octane.

2. A method for producing hydrocarbons comprising:
contacting a hydrocarbon feedstock comprising normal paraffins having 10 or more carbon atoms with the hydroisomerization catalyst of claim 1 in the presence of hydrogen.

3. A method for producing lubricant base oil comprising:
contacting a hydrocarbon feedstock comprising normal paraffins having 10 or more carbon atoms with the hydroisomerization catalyst of claim 1 in the presence of hydrogen,
under conditions in which the conversion of the normal paraffins, which is defined by the Expression (I), becomes substantially 100% by mass:

$$\text{Normal paraffin conversion (\%)} = \left[1 - \left(\frac{\text{Total mass of normal paraffins equal to or greater than } Cn \text{ contained in contacted hydrocarbon feedstock}}{\text{Total mass of normal paraffins equal to or greater than } Cn \text{ contained in hydrocarbon feedstock yet to be contacted}}\right)\right] \times 100 \quad (I)$$

where $Cn$ is the lowest number of carbon atoms of normal paraffins having 10 or more carbon atoms contained in the hydrocarbon feedstock yet to be contacted.

4. The method for producing lubricant base oil according to claim 3 further comprising:
hydrofinishing and vacuum-distilling the hydrocarbon feedstock after the hydrocarbon feedstock is contacted with the hydroisomerization catalyst.

5. The method for producing lubricant base oil according to claim 3,
wherein the hydrocarbon feedstock is at least one selected from: atmospheric residues; vacuum residues; a vacuum gas oil; a slack wax; and a Fischer Tropsch synthetic wax.

\* \* \* \* \*